US009874529B2

(12) United States Patent
Morrison, III et al.

(10) Patent No.: US 9,874,529 B2
(45) Date of Patent: Jan. 23, 2018

(54) APPARATUS AND METHOD FOR INSPECTION OF AN END REGION SUPPORTED STEERING COLUMN ASSEMBLY

(71) Applicant: NSK AMERICAS, INC., Ann Arbor, MI (US)

(72) Inventors: George Morrison, III, Taylor, MI (US); Ty Alan Brown, Clarinda, IA (US); Timothy Brian Rood, Ann Arbor, MI (US)

(73) Assignee: NSK Americas, Inc., Ann Arbor, MI (US)

( * ) Notice: Subject to any disclaimer, the term of this patent is extended or adjusted under 35 U.S.C. 154(b) by 0 days.

(21) Appl. No.: 15/116,612

(22) PCT Filed: Feb. 4, 2015

(86) PCT No.: PCT/US2015/014430
§ 371 (c)(1),
(2) Date: Aug. 4, 2016

(87) PCT Pub. No.: WO2015/120030
PCT Pub. Date: Aug. 13, 2015

(65) Prior Publication Data
US 2016/0349190 A1    Dec. 1, 2016

Related U.S. Application Data

(60) Provisional application No. 61/935,421, filed on Feb. 4, 2014.

(51) Int. Cl.
*G01N 21/00* (2006.01)
*G01N 21/95* (2006.01)
(Continued)

(52) U.S. Cl.
CPC ......... *G01N 21/9515* (2013.01); *B62D 65/02* (2013.01); *G01B 11/00* (2013.01);
(Continued)

(58) Field of Classification Search
CPC ............ G01N 21/9515; G01N 21/952; G01N 2021/888; G01N 2021/06113; G01N 2021/103
See application file for complete search history.

(56) References Cited

U.S. PATENT DOCUMENTS 4,576,482 A * 3/1986 Pryor ................. G01B 11/2433
209/538
5,162,659 A    11/1992 Diamond et al.
(Continued)

FOREIGN PATENT DOCUMENTS

DE    102004007830 A1    9/2005
WO        03/058164 A1    7/2003

OTHER PUBLICATIONS

International Search Report and Written Opinion for international application No. PCT/US2015/014430, dated May 22, 2015.

*Primary Examiner* — Michael P Stafira
(74) *Attorney, Agent, or Firm* — The Dobrusin Law Firm, P.C.

(57) ABSTRACT

An apparatus (110) (and associated method) for inspecting a steering column assembly (10) including a motor (114*a*) driven drive sleeve (128) supported in a headstock (114) and having a longitudinal axis, and being adapted for receiving and engaging a portion of the steering column assembly, and at least one optical scanning device (160*a*, 160*b*, 160*c*) adapted to optically scan a feature of interest of the steering column assembly (10) while the shaft of the steering column assembly (10) is rotated for gathering data for identifying (Continued)

one or more deviations from one or more predetermined values for the feature of interest.

20 Claims, 13 Drawing Sheets

(51) Int. Cl.
    *G01N 21/952* (2006.01)
    *B62D 65/02* (2006.01)
    *G01B 11/00* (2006.01)
    *G01N 21/88* (2006.01)
    *G01B 5/00* (2006.01)

(52) U.S. Cl.
    CPC ......... *G01N 21/952* (2013.01); *G01B 5/0025* (2013.01); *G01N 2021/888* (2013.01); *G01N 2201/06113* (2013.01); *G01N 2201/103* (2013.01)

(56) References Cited

U.S. PATENT DOCUMENTS

| | | |
|---|---|---|
| 5,267,381 A | 12/1993 | Wright et al. |
| 5,426,309 A | 6/1995 | Davidson et al. |
| 7,308,130 B2 * | 12/2007 | Pahk ............... G01B 11/00 134/21 |
| 7,499,812 B2 | 3/2009 | Ersue et al. |
| 2002/0101595 A1 * | 8/2002 | Johnson ............ G01B 11/245 356/602 |
| 2013/0170734 A1 | 7/2013 | Uchiyama et al. |

* cited by examiner

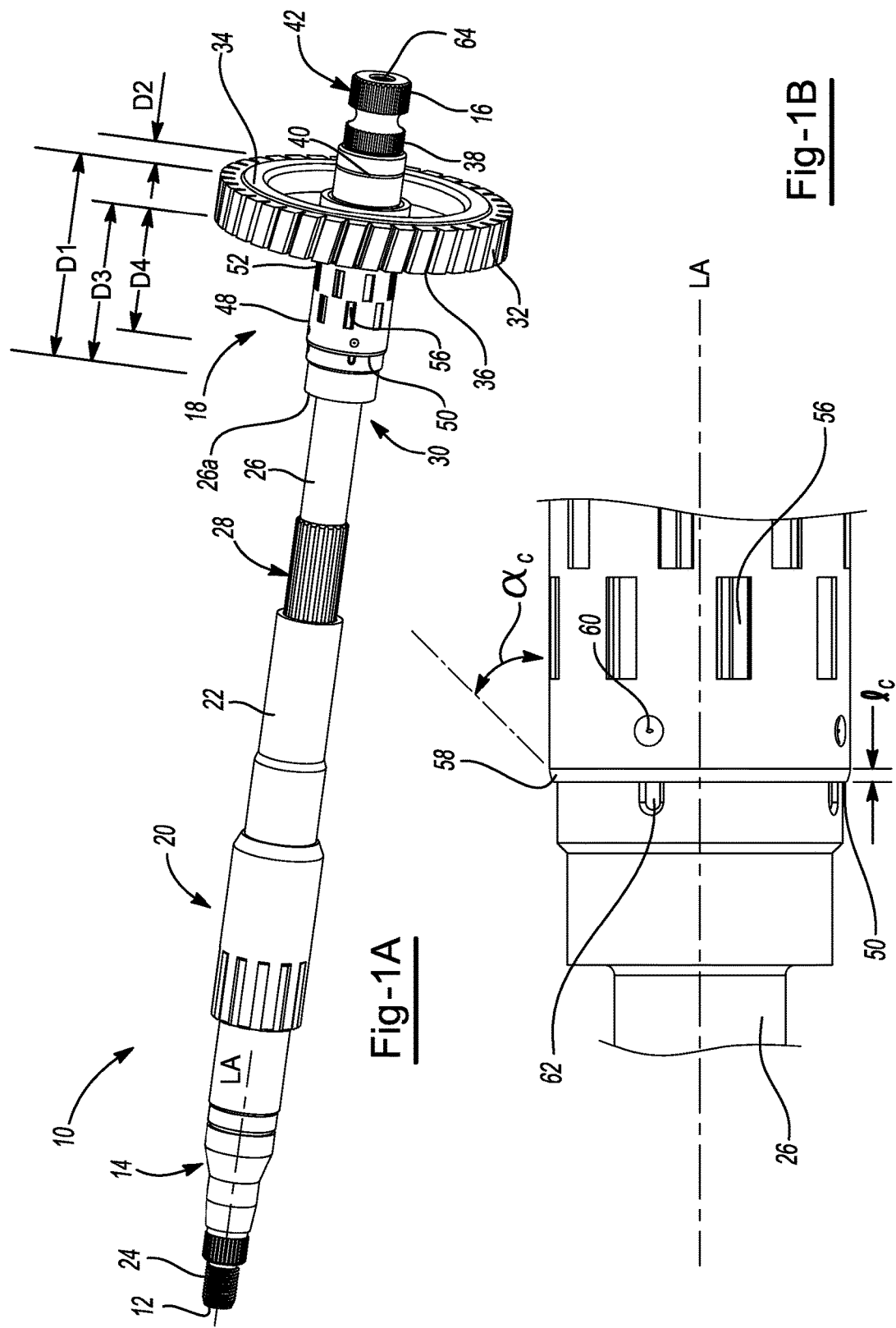

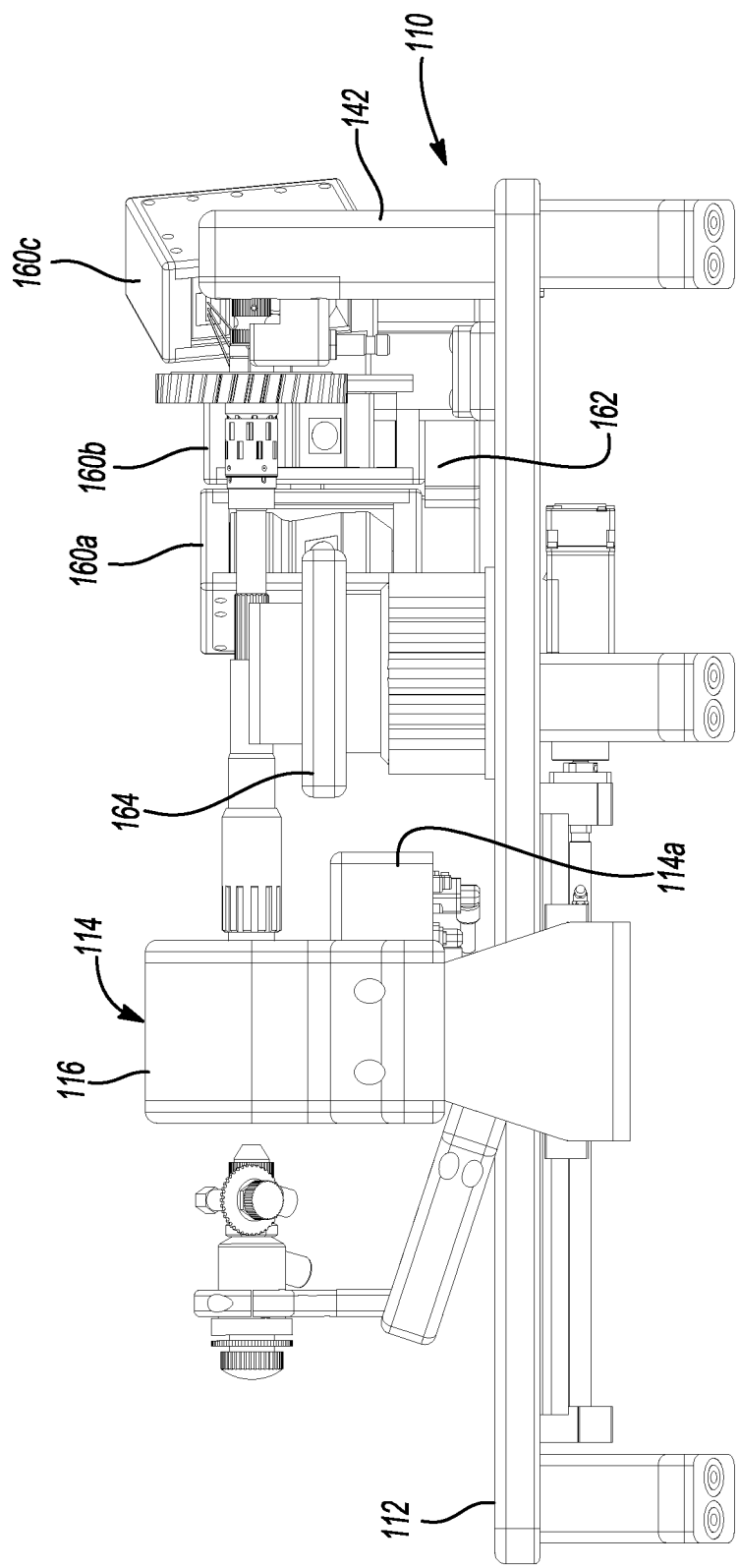

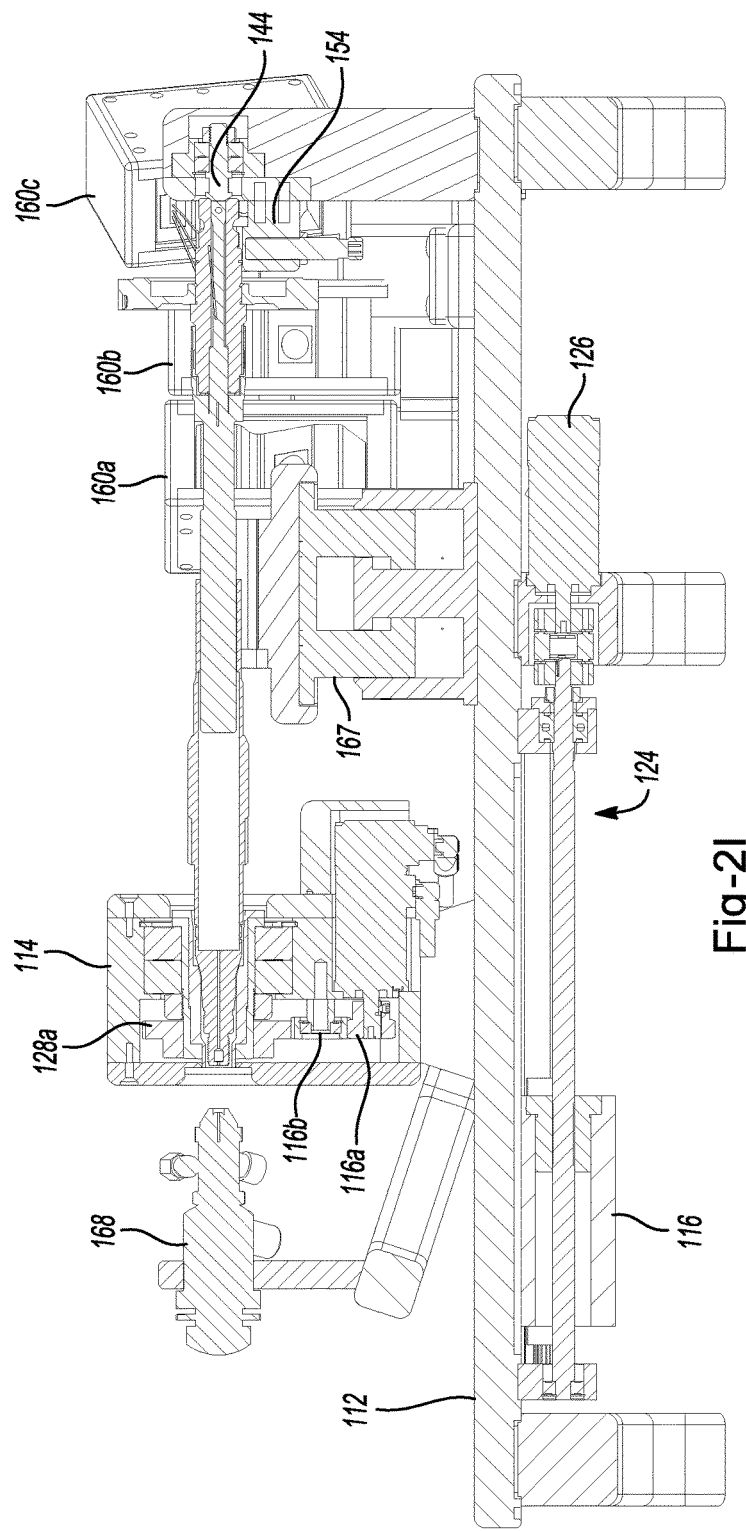

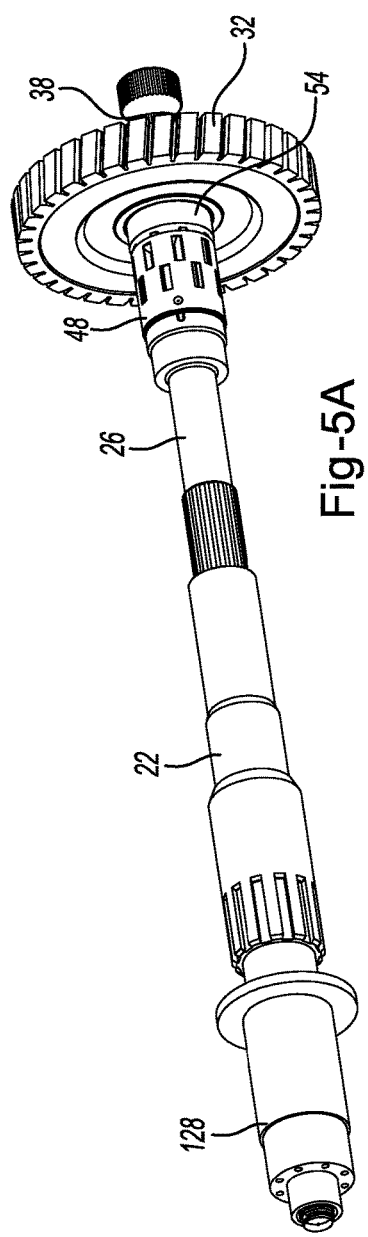
Fig-5A
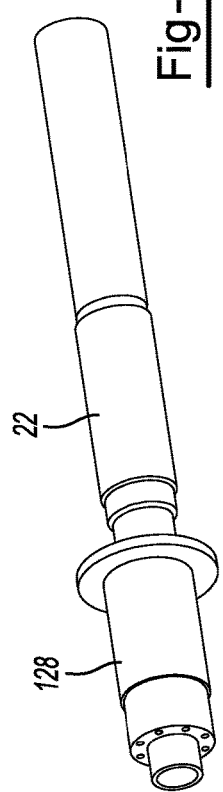
Fig-5B
Fig-5C
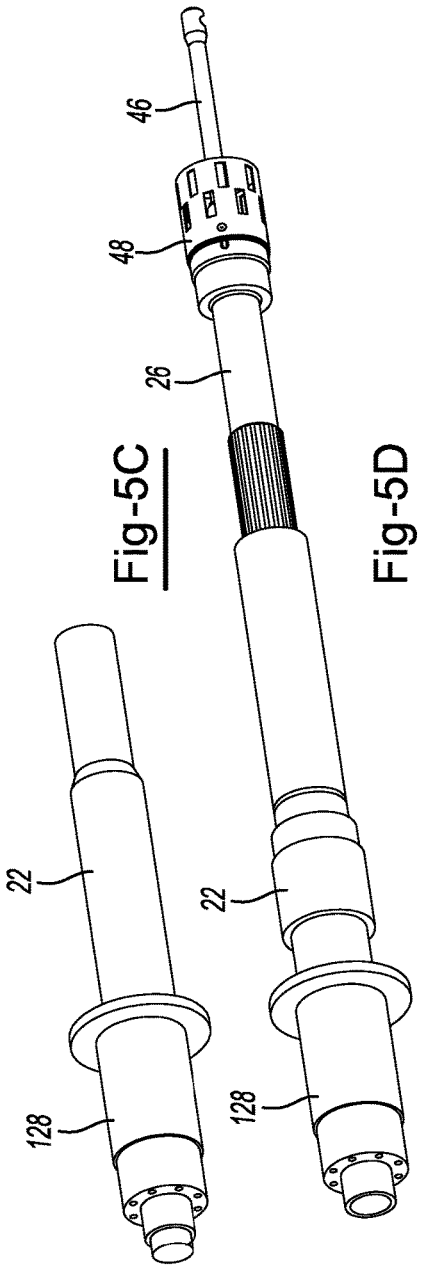
Fig-5D

APPARATUS AND METHOD FOR INSPECTION OF AN END REGION SUPPORTED STEERING COLUMN ASSEMBLY

CLAIM OF BENEFIT OF FILING DATE AND PRIORITY

The present application claims the benefit of the filing date of, and priority to, U.S. application Ser. No. 61/935,421, filed Feb. 4, 2014, which is hereby incorporated by reference in its entirety. The present application is also related to U.S. application Ser. No. 61/935,419, filed Feb. 4, 2014, which is hereby incorporated by reference in its entirety.

FIELD

In general, the present teachings relate to an apparatus and method for inspection of a steering column assembly before installation into a transportation vehicle, More particularly, the present teachings relate to an apparatus and method for non-contact inspection of a steering column assembly for an automotive vehicle while the steering column assembly is rotatably supported at one or both of its end portions.

BACKGROUND

In the manufacture of steering column assemblies, there are often a number of subassemblies or components that require assembly with each other. For proper operation, many of the subassemblies or components are adapted for rotation about a longitudinal axis upon installation into a vehicle for which it is intended. It is important in the manufacture of steering column assemblies that individual subassemblies or components are properly attached to one another. This is often achieved by one or more crimping, staking or other plastic deformation operations by which a sleeve, a tube, a disk or some other generally cylindrical and hollow object is connected around a shaft, or some other generally cylindrical component so that the connected parts resist longitudinal separation, resist radial displacement, or both. Though it is possible for an assembly line worker to perform a visual and/or manual inspection for quality assurance, such an inspection leaves open the possibility of some subjectivity from one worker to another and may lead to potentially inconsistent results.

There is a need for an automated approach to the inspection of steering column assemblies ("steering column assemblies" as used herein contemplate not only final steering column assemblies adapted for installation into a vehicle, but also subassemblies that are incorporated into final steering column assemblies) before installation of the same into a vehicle. There is a particular need for a non-contact approach to the inspection of steering column assemblies (e.g., joints between components of the assemblies) by which the device that conducts the inspection does so without making contact with the steering column assemblies while being inspected, There is also a need for an approach to steering column assemblies that allows for rotation of steering column assemblies, but which avoids contact with components of the steering column assemblies in a manner that would potentially damage the steering column assemblies. There also is a need to manage inventory being manufactured and inspected to help assure that assemblies that fail to meet certain criteria are segregated from those assemblies that do meet such criteria.

The following U.S. patent documents may be related to the present teachings: Published U.S. Patent Application Nos. 20020101595 and 20130170734, and U.S. Pat. Nos. 5,162,659; 5,267,381; 5,426,309, all of which are incorporated by reference herein for all purposes.

SUMMARY

The present teachings make use of a simple, yet elegant, approach to non contact inspection of a steering column assembly by which the steering column assembly is rotatably supported at one or both of its end regions, and is rotated about a longitudinal axis so that profile data can be gathered about a feature of interest by an optical detection device and used to assure the presence of the feature of interest and/or to determine if the feature of interest meets certain predefined criteria. As gleaned from the following, the teachings contemplate, generally, an apparatus (and associated method) for inspecting a steering column assembly, including a motor driven drive sleeve having a longitudinal axis adapted for receiving and engaging a portion of the steering column assembly, and at least one optical scanning device (which desirably is spaced apart from the steering column assembly under inspection) adapted to optically scan a feature of interest of the steering column assembly while the shaft of the steering column assembly is rotated for gathering data for identifying one or more deviations from one or more predetermined values for the feature of interest.

In one aspect, the present teachings pertain generally to an apparatus for inspecting a steering column assembly having a longitudinal axis, a first end, a first end portion extending from the first end along the longitudinal axis from the first end (and which may include a telescopic shaft subassembly or a component thereof, such as an outer steering wheel interface shaft tube that has an associated steering wheel interface), a second end, and a second end portion including and/or extending from the second end toward the first end along the longitudinal axis (and which may include a stub shaft). The apparatus includes at least one support structure having a longitudinal axis. A headstock may be mounted (e.g., fixedly or translatably mounted) on the at least one support structure and includes at least one motor The headstock may thus be adapted to translate relative to the at least one support structure (e.g., via a linear actuator driven by a suitable motor, such as a servo motor) generally along the longitudinal axis of the at least one support structure. The headstock may be able to translate longitudinally and/or transversely, or along another axis of the at least one support structure. A drive sleeve having a longitudinal axis is supported in the headstock for rotation by the at least one motor. The drive sleeve includes an inner wall surface that is adapted for receiving and engaging the first end portion of the steering column assembly.

An optional tailstock (which may be carried on the support structure or on another support structure) may optionally include a roller pin having a longitudinal axis. The longitudinal axis of the roller pin is substantially juxtaposed with the longitudinal axis of the drive sleeve. The roller pin has an outer surface that is adapted for engaging the second end portion of the steering column assembly and for bearing against the second end portion during rotation of the shaft so that the shaft is suspended relative to the at least one support structure. One or both of the headstock or the tailstock may be translatably mounted relative to the other for bringing them together or moving them apart from each other.

At least one optical scanning device (which may be carried by the support structure, its own support structure, or the support structure of the optional tailstock) is also included. The at least one optical scanning device is adapted to scan for the presence or absence of a feature of interest and/or for a characteristic of a feature (e.g., a surface feature) of interest of the steering column assembly while the shaft of the steering column assembly is rotated for gathering data, such as for identifying one or more deviations from a predetermined value for the feature of interest. In this regard, it is envisioned that the at least one optical scanning device is adapted to emit a beam and the at least one optical scanning device is oriented so that the beam is aimed at the feature of interest of the steering column assembly. For an apparatus that includes the optional tailstock and roller pin, the apparatus is such that, upon receiving and engaging the first end portion of the shaft of the steering column assembly, the headstock is adapted for actuation to translate it toward the roller pin so that the roller pin engages the second end portion of the steering column assembly and the steering column assembly is rotated while being scanned by the at least one optical scanning device, The teachings also contemplate a non-contact method of inspecting a steering column assembly. The inspection is performed after manufacture of the steering column assembly and prior to installation into a vehicle. The method may employ steps of engaging a portion (e.g., a first end portion) of the steering column assembly with an interior surface of a drive sleeve (e.g., so that line or plane contact is made with a portion of the steering column assembly generally continuously or intermittently about the perimeter of the assembly). While the portion (e.g., first end portion) is engaged with the drive sleeve, it is rotated (e.g., by being driven by a motor) while being scanned by at least one optical scanning device. A step is employed of comparing data obtained by the at least one optical scanning device with one or more known and predetermined values for a reference steering column assembly. For example, the comparing step may perform a comparison of relative locations of a plurality of features of interest in a steering column assembly under inspection with known values for relative locations of corresponding features obtained from scanning a steering column assembly that has been predetermined to satisfy established quality criteria. Based upon the comparing step, an inspected steering column assembly can either be approved or rejected, and conforming and non-conforming steering column assemblies can be segregated from each other.

A method of the present teachings contemplates use of the apparatus of the present teachings for non-contact inspection of a steering column assembly that is specifically designed and intended to generally include a worm-wheel at the second end portion, and a sensor sleeve fixed in position between the worm-wheel and the first end. The sensor sleeve may be attached to a shaft with a crimp and/or a dimple that penetrates into a groove of the shaft. Thus, the method includes inspecting steering column assemblies for one or any combination of the following features of interest: dimple location, dimple depth, dimple location relative to a groove in the spline shaft portion, sensor sleeve appearance, sensor sleeve runout, sensor sleeve peripheral crimp appearance, sensor sleeve crimp angle, distance from a location on the sensor sleeve to a shoulder on the spline shaft portion, location of a c-ring groove, distance of a c-ring groove relative to a surface on the worm-wheel, position of the sensor sleeve relative to a worm-wheel surface, distance from a location on the sensor sleeve to a worm-wheel surface, location of the worm-wheel relative to a predetermined location in the spline shaft portion, or any combination of the foregoing.

The present teachings provide a number of technical benefits, including but not limited to the ability to consistently and reproducibly inspect steering column assemblies for assuring that the assemblies meet predefined criteria, the ability to inspect a variety of different steering assemblies without the need to modify any hardware of an inspection apparatus, the ability to inspect steering column assemblies before installation into a vehicle (e.g., a location of manufacture or storage), the ability to identify nonconforming steering column assemblies before additional costly assembly steps are performed and to thereby help reduce scrap rates of expensive assemblies, or any combination of the foregoing.

BRIEF DESCRIPTION OF THE DRAWINGS

FIG. 1A is a perspective view of an illustrative steering column assembly that may be inspected in accordance with the present teachings.

FIG. 1B is an enlarged side view of a portion of the assembly of FIG. 1A.

FIG. 2E is a side view of the apparatus of FIG. 2A.

FIG. 2I is a side sectional view of the apparatus of FIG. 2A.

FIG. 2J is a side view of an illustrative roller pin.

FIGS. 5A, 5B, 5C and 5D are a series of perspective views corresponding respectively with the views of FIGS. 4A-4D.

DETAILED DESCRIPTION

Figure 2A:
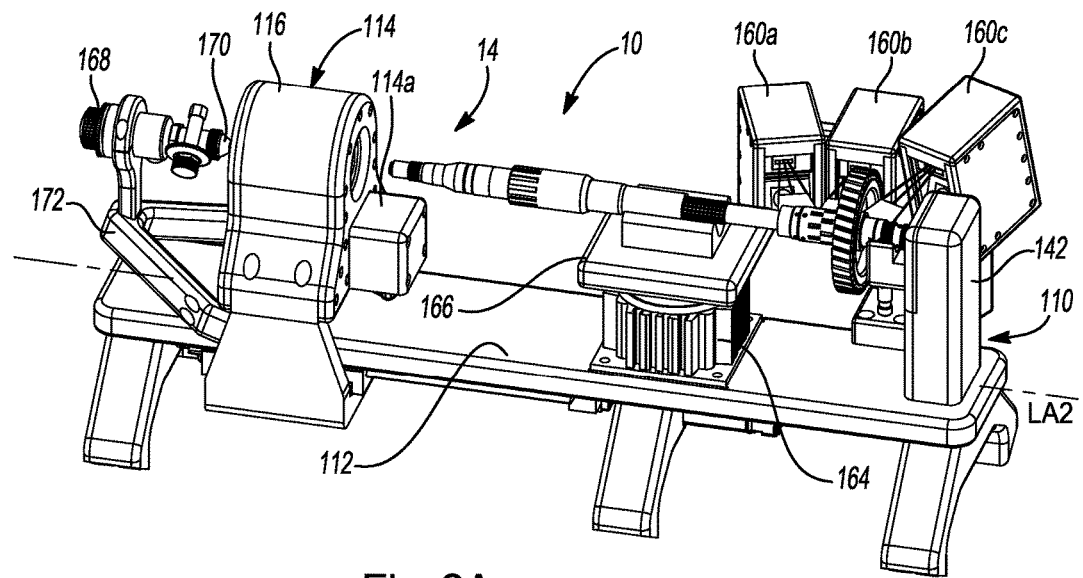
FIG. 2A is a perspective view of an illustrative apparatus in accordance with the present teachings in a first unloaded position.
Figure 2B:
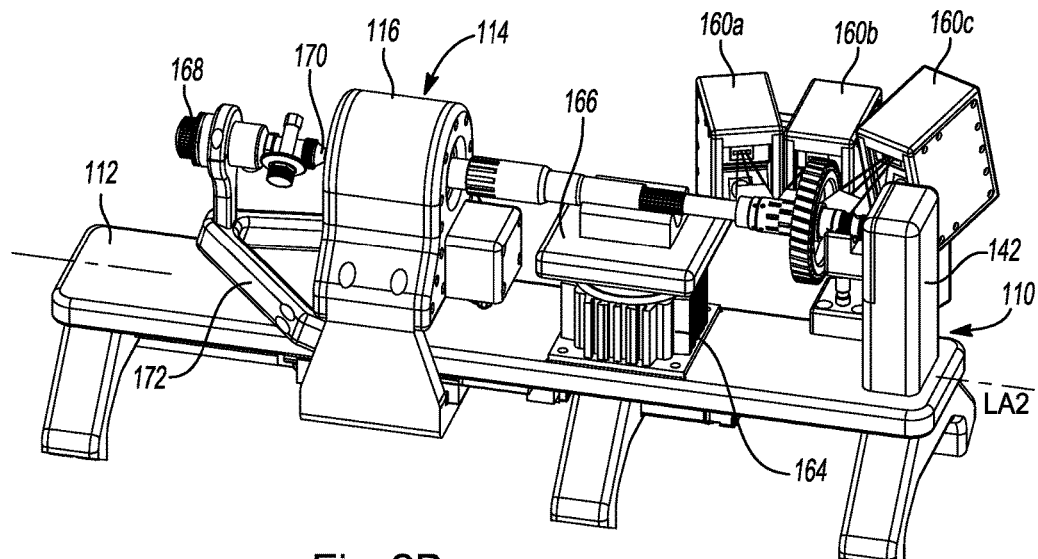
FIG. 2B is a perspective view of an illustrative apparatus in accordance with the present teachings in a second loaded position.
Figure 2C:
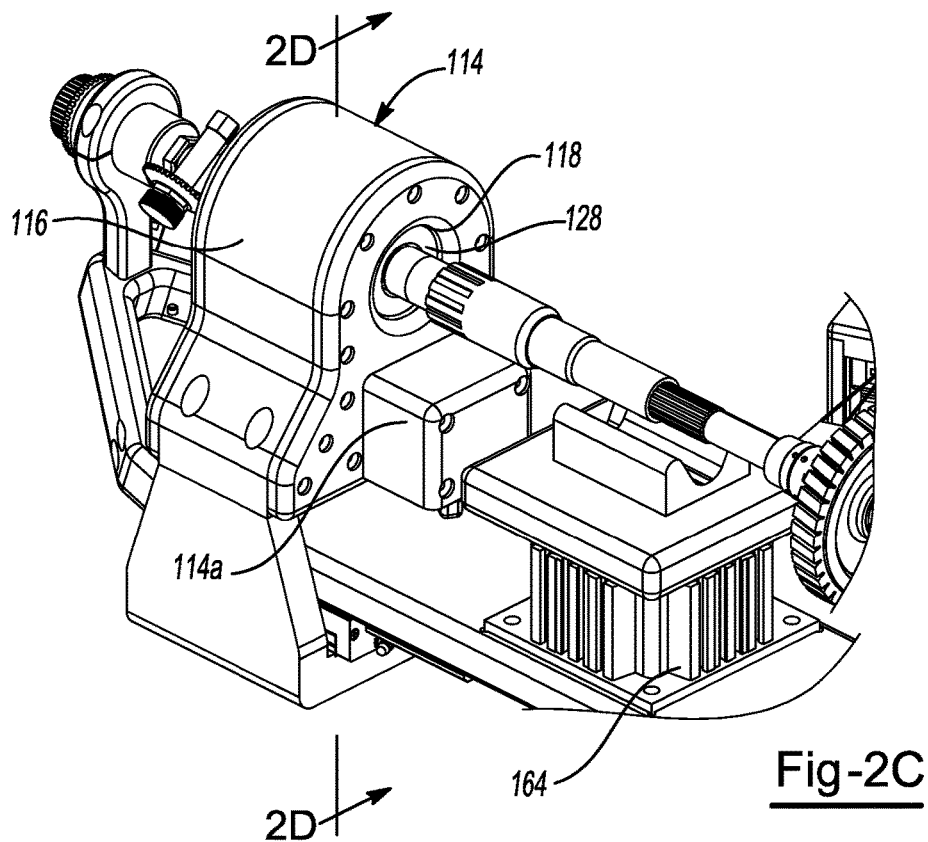
FIG. 2C is an enlarged partial perspective view of the apparatus of FIG. 2A in a loaded position.
Figure 2D:
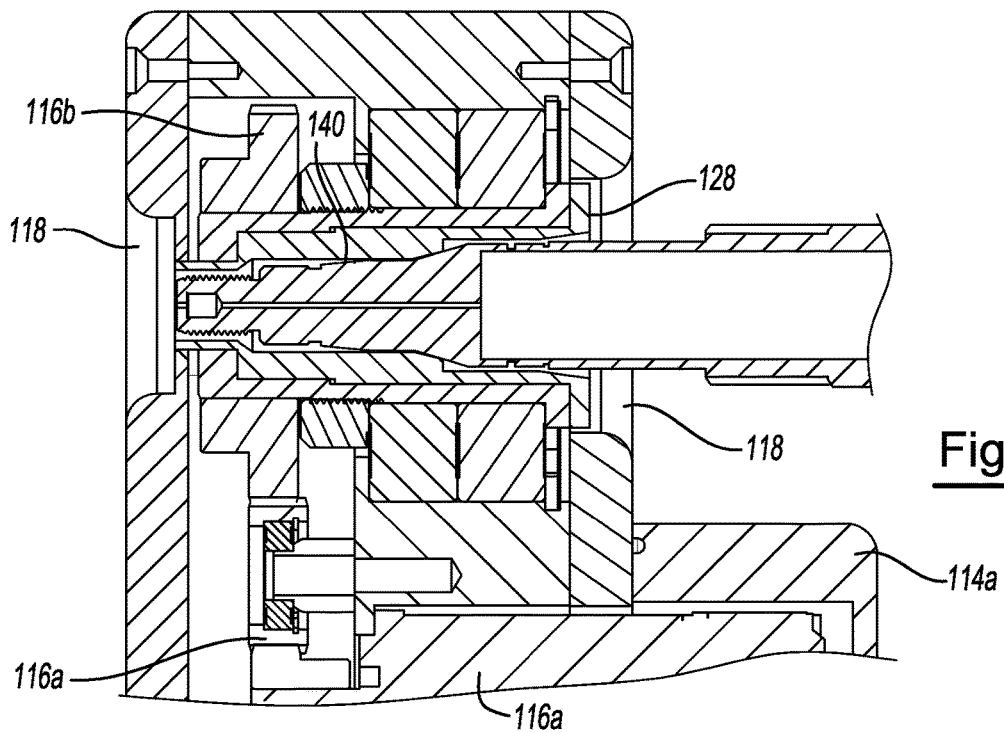
FIG. 2D is an enlarged partial side section view of the apparatus of FIG. 2A in a loaded position.
Figure 2F:
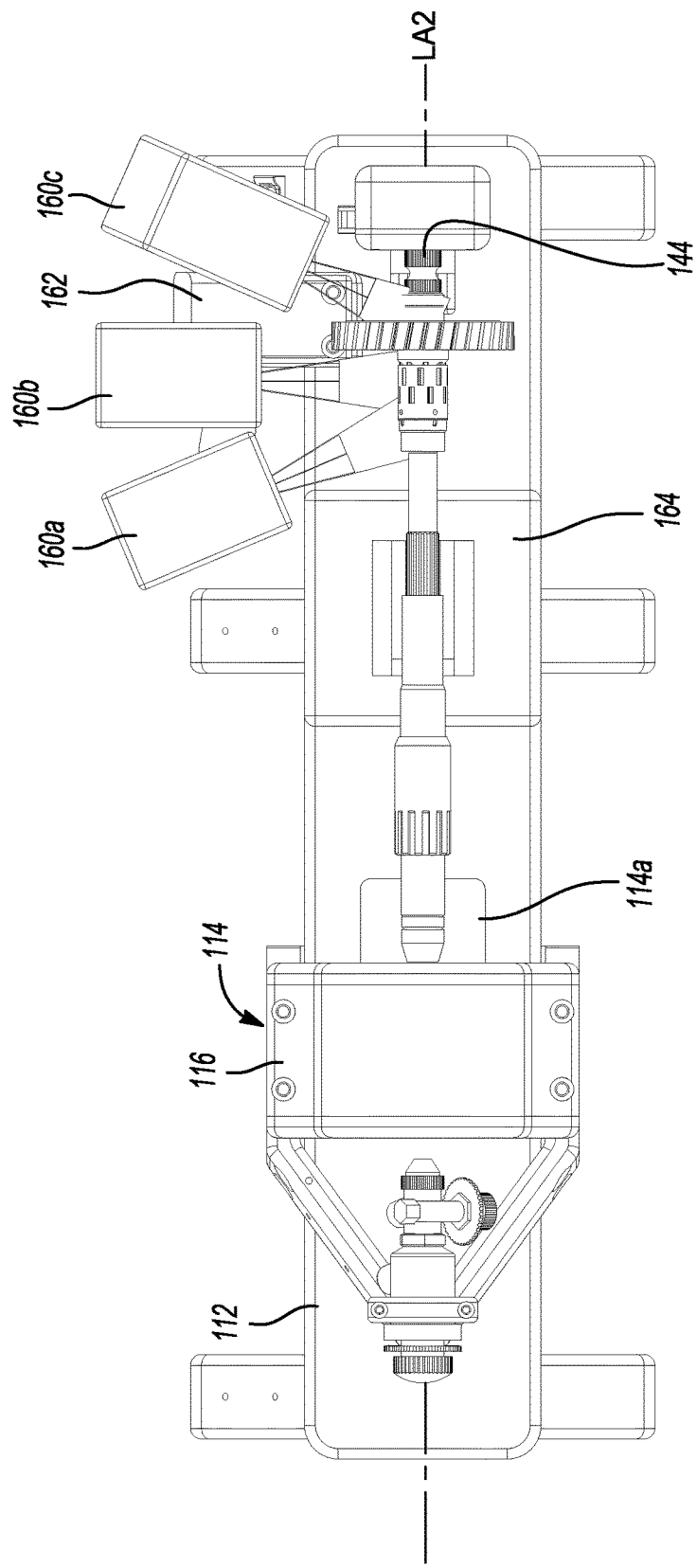
FIG. 2F is a top view of the apparatus of FIG. 2A.
Figure 2G:
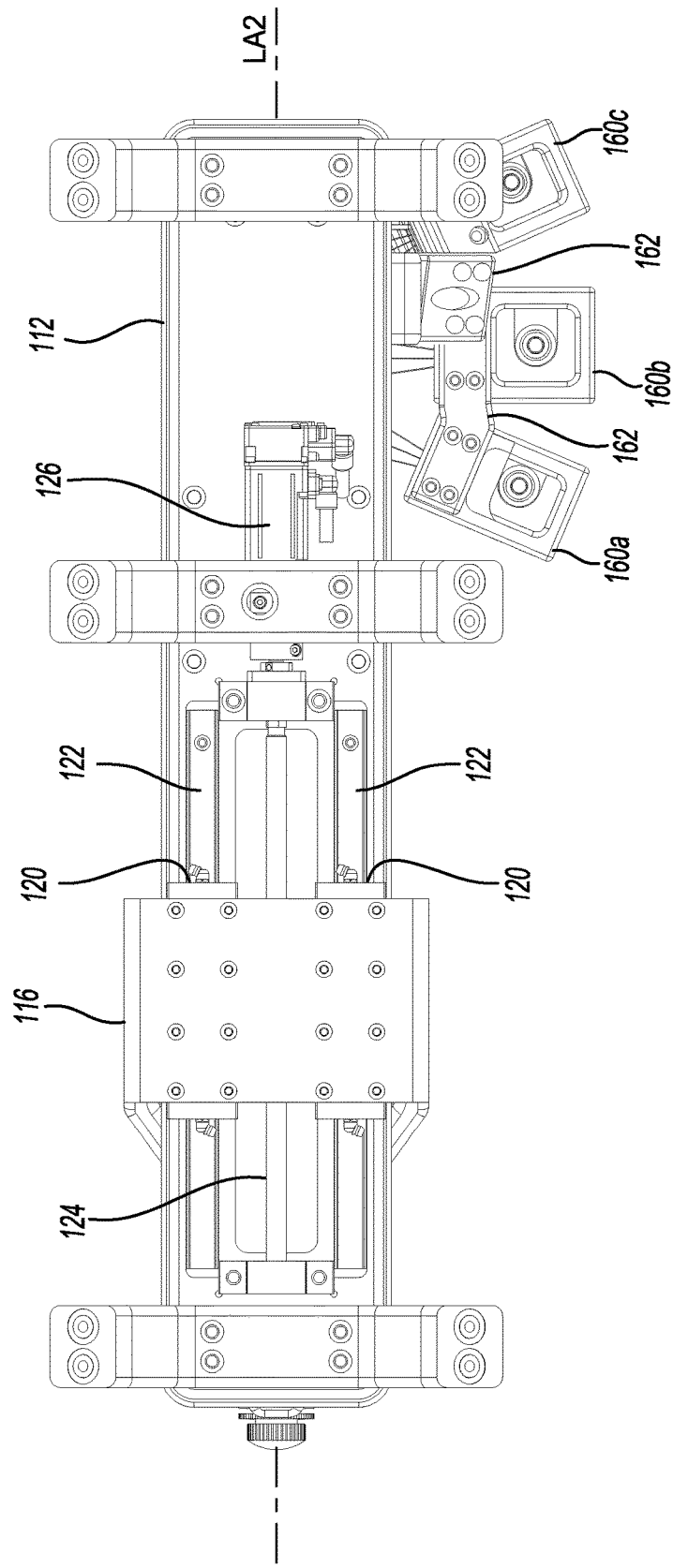
FIG. 2G is a bottom view of the apparatus of FIG. 2A.
Figure 2H:
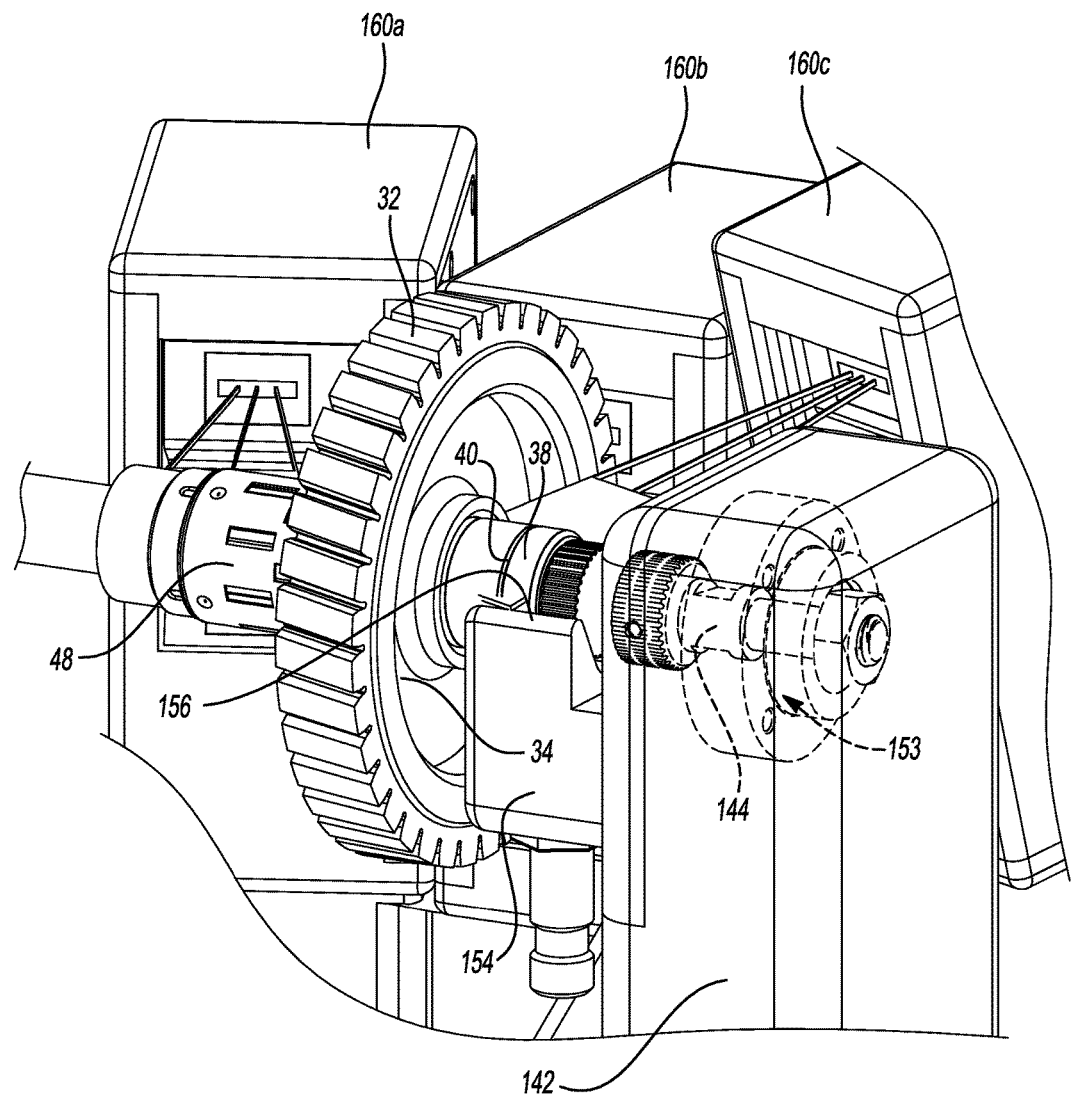
FIG. 2H is an enlarged partial transparent view of an end region of the apparatus of FIG. 2A, to further illustrate the roller pin engaging a steering column assembly.

As required, detailed embodiments of the present teachings are disclosed herein; however, it is to be understood that the disclosed embodiments are merely exemplary of the teachings that may be embodied in various and alternative forms. The figures are not necessarily to scale; some features may be exaggerated or minimized to show details of particular components. Therefore, specific structural and functional details disclosed herein are rot to be interpreted as limiting, but merely as a representative basis for teaching one skilled in the art to variously employ the present invention.

In general, and as will be appreciated from the description that follows, the present teachings pertain to pre-vehicle installation quality inspection of steering column assemblies to assure that the assemblies being inspected have the intended design features and meet the intended design criteria. The steering column assemblies generally are envisioned to have an intended design such that the assemblies have a longitudinal axis and a telescoping shaft assembly. The telescoping shaft assembly has a first end that defines a steering wheel interface. A worm-wheel for interfacing with a power assist device is mounted on a stub shaft (which defines a second end portion and includes a second end of the steering column assembly) that is joined to the telescoping shaft assembly. The stub shaft may be suitably coupled to an intermediate shaft for actuating a rack and pinion assembly of a vehicle. A sensor sleeve surrounds sensing hardware and is attached (e.g., crimped with a peripheral crimp) to the telescoping shaft assembly. A dimple in the sensor sleeve that penetrates a recess in the telescoping shaft assembly may be employed to aid the sensor sleeve in resisting rotation. As gathered from the above, the present teachings thus pertain generally to an apparatus and method for inspecting a steering column assembly having a longitudinal axis, a first end, a first end portion extending from the first end along the longitudinal axis from the first end, a second end, a second end portion including and/or extending from the second end toward the first end along the longitudinal axis. One object of the teachings thus is to help assure that a steering column assembly being inspected has the intended design features, such as the features described above generally, and more particularly addressed herein.

As indicated, in one aspect, the present teachings pertain generally to an apparatus that includes at least one support structure having a longitudinal axis. A headstock is mounted (e.g., it may be translatably mounted) on the at least one support structure and includes at least one work-piece drive motor. The motor may be adapted to rotate a steering column assembly that is loaded in the apparatus about the longitudinal axis of the steering column assembly. The headstock may include a shroud that contains the motor or a drive mechanism associated with the motor. The shroud may substantially surround the headstock, but may include openings at opposing ends. In that way, the headstock will be able to receive the first end portion of the steering column assembly and will also expose the first end so that the end is able to the coated with a colorant, dye, or other detectable coating that denotes whether or not the steering column assembly has passed inspection. The shroud may extend around the support structure. The shroud may include one or more guide structures adapted to translate along one or more longitudinally oriented tracks associated with the support structure, such as on the underside of the support structure. In this manner, it may be possible to help direct the travel of the headstock relative to the support structure. The at least one work-piece drive motor may be integrated with the headstock. The at least one work-piece drive motor may be separate from the head stock (e.g., at a remote location). A belt drive may enable the motor to be located in one location (e.g., at or near the center of the at least one support structure), while the headstock is located at an end of the at least one support structure. The headstock may otherwise be adapted to be driven relative to the at least one support structure (e.g., via a linear actuator driven by a suitable motor, such as a servo motor) generally along the longitudinal axis of the at least one support structure. The motors for use in accordance with the present teachings may be a servo motor. By way of illustration, motors herein may have the characteristics of a motor available commercially from Omron (e.g., under the number R88M-K0030LS2).

A drive sleeve having a longitudinal axis is supported in the headstock for rotation by the at least one work-piece drive motor. The work-piece drive motor may include an output shaft that has a gear, a roller, or some other drive structure that meshes with or otherwise engages an opposing gear or drive surface that surrounds the drive sleeve. Thus, the work-piece drive motor may rotate for causing a steering column assembly that is supported in the drive sleeve to rotate about the longitudinal axis of the steering column assembly. The work-piece drive motor may rotate for causing a steering column assembly that is supported in the drive sleeve to rotate about the longitudinal axis of the steering column assembly. For example, the drive sleeve may be surrounded along a portion of its length by a suitable bearing. The drive sleeve may have a suitable gear that generally surrounds the drive sleeve and is driven by a gear associated with the output shaft of the work-piece drive motor or an intermediate idler gear. The drive sleeve gear, any output shaft gear and any idler gear may be adapted to rotate in a common plane and about an axis that is generally parallel with the axis of the steering column assembly being inspected.

The drive sleeve will include a longitudinal axis that is generally parallel with (or coaxial with) the longitudinal axis of the steering column assembly that it receives, a first end and a second end At the first end, there may be an opening, so that a through passage is defined along the length of the drive sleeve. At the second end there may be a peripheral flange The drive sleeve will include an inner wall surface that is adapted for receiving and engaging the first end portion of the steering column assembly. The inner wall surface may include one or a plurality of cylindrical wall segments, one or a plurality of frusto-conical wall segments, or a plurality of arcuate wall segments, or any combination thereof. The inner wall surface desirably will include a plurality of wall segments, each having a cross-sectional area (taken transverse to the longitudinal axis of the drive sleeve) that progressively reduces in size from the second end toward the first end, for at least a portion of the length of the drive sleeve. One or more shoulders may be defined at the intersection of successive wall segments. As a result of having such inner wall structure, the drive sleeve is able to receive the first end portion of a variety of different steering column assemblies, each having a differently configured and/or differently dimensioned first end portion. The shoulders allow such steering column assemblies to engage the drive sleeve at a location along the first end portion. The drive sleeve may have a continuous inner wall surface. The drive sleeve may have an intermittent wall surface. The drive sleeve may include a plurality of jaws that grip the end portion of the steering column assembly.

The drive sleeve may be made of a softer material than the material of the first end portion of the steering column assemblies supported therein, so that during loading and inspecting, damage to the steering column assemblies is avoided. The drive sleeve may have a surface texture, may be made of a material having a sufficiently low coefficient of friction, or both, so that when the drive sleeve is rotatably driven by the work-piece drive motor, the first end portion of the steering column assembly being inspected remains engaged with the drive sleeve. For example, the drive sleeve may be a polymeric material (e.g., an elastomeric material). The drive sleeve may engage the periphery of a tapered portion of the first end portion. For example, it may engage a tapered wall of an outer tube of the steering column assembly (e.g., an outer tube of a telescopic steering column assembly).

An optional tailstock may be employed (which may be carried on the support structure or on another support structure), which may carry a suitable roller pin, e.g, an idler pin, having a longitudinal axis. The roller pin may be supported for rotation (e.g., by way of a suitable bearing, such as a roller bearing that surrounds the roller pin and is fixed in position in the tailstock). The optional tailstock may be fixed in position on its support structure, or it may be longitudinally translatable along the apparatus. Thus, the headstock and the tailstock may be translatable relative to each other. The longitudinal axis of the roller pin is substantially juxtaposed with the longitudinal axis of the drive sleeve. The roller pin has an outer surface that is adapted for engaging the second end portion of the steering column assembly and for bearing against the second end of the steering column assembly during rotation of the shaft so that the shaft is suspended relative to the at least one support structure. The roller pin may include a free end that engages the second end of a steering column assembly being inspected. The roller pin may be dimensioned so that it can penetrate into a recess of the second end of the steering column assembly. For instance, the roller pin may be supported for rotation about its longitudinal axis (e.g., the roller pin may be supportably carried by a suitable bearing associated with the tailstock, such as at least one round bearings supported by a bearing block). The roller pin may have a free end that is rounded or at least partially conical (e.g., it may have a flat portion and a conical portion). It thus may have a tapered wall portion. The tip of the roller pin may have a ball disposed therein.

A work-piece end support platform may be located next to or as part of the tailstock. The work-piece end support platform may be carried by the same support structure as the tailstock, or a different support structure. The work-piece end support platform may have an upper surface that includes a concave depression, a v-shaped depression or some other depression adapted to support a second end portion of a steering column assembly when the steering column assembly is initially placed for inspection on the apparatus. The upper surface may be located at a position that is offset relative to the longitudinal axis of the roller pin. The upper surface may be located at a position such that when the second end portion of a steering column assembly is initially placed thereon, and the first end portion becomes engaged by the drive sleeve, the longitudinal axis of the steering column assembly is initially at an angle of about 1 to about 20°, and more preferably about 2 to about 10° relative to the longitudinal axis of the drive sleeve. For embodiments that include a tailstock as described herein, as the headstock and/or the tailstock are translated relative to each other, the second end of the steering column assembly will contact the roller pin and bear against the roller pin until the roller pin becomes located within the recess of the second end. As a result, the second end will become elevated from the upper surface of the work-piece end support platform.

At least one optical scanning device (which may be carried by the support structure, its own support structure, or the support structure of the tailstock) is also included. The at least one optical scanning device is adapted to scan a feature (e.g., a surface feature) of interest of the steering column assembly while the shaft of the steering column assembly is rotated for gathering data for identifying one or more deviations from a predetermined value for the feature of interest. In this regard it is envisioned that the at least one optical scanning device is adapted to emit a beam and the at least one optical scanning device is oriented so that the beam is aimed at the feature of interest of the steering column assembly. The apparatus may be such that, upon receiving and engaging the first end portion of the shaft of the steering column assembly, the headstock is adapted for actuation to translate it toward the roller pin so that the roller pin engages the second end portion of the steering column assembly and the steering column assembly is rotated while being scanned by the at least one optical scanning device.

The at least one optical scanning device may be a suitable in-line profile measurement device. The at least one optical scanning device may include a light beam emitter (e.g., a laser beam emitter), which may be adapted to emit a generally diffuse beam (e.g., the beam may be emitted so that, at the location where it reflects off a steering column assembly, a linear segment (e.g., a blue linear segment) is visible). For example, it may include a blue laser beam emitter (i.e., it emits blue light at a wavelength of about 360 to about 480 nm (e.g., at about 405 nm)). The at least one optical scanning device may include a suitable detector positioned relative to the light beam emitter for detecting reflection from a surface of the steering column assembly being inspected. The detector may include a solid state detector, such as a complementary metal oxide semiconductor detector. The at least one optical scanning device may include one or more lenses (e.g., at least one cylindrical lens) for focusing the beam from the emitter source, and/or a two dimensional lens device (e.g., a lens device that may include one or a plurality of lenses that can concentrate light entering it from various angles to a single point, such as an Ernostar lens) for receiving at least a portion of the light that is reflected from the steering column subassembly. The at least one optical scanning device may include a suitable processor adapted to acquire data from the detector and output such data to a suitable display device. The processor (or another processor) may be suitably programmed to perform a comparison of data acquired from inspecting a steering column assembly with predetermined values (e.g., values stored in memory associated with the processor performing the comparison) or other data about a known reference steering column assembly. The processor may be suitably programmed to output the results of an inspection of a steering column assembly. In this regard, the processor may be suitably programmed to cause an audible alarm, a visual alarm, or both, to issue if a steering column assembly passes or fails an inspection. The processor may be suitably programmed to identify one or more features of interest that fails to meet a predetermined criteria for such feature. An example of a commercially available optical scanning device is Model No. LJ-V7080, available from Keyence Corporation of America. The scanning device may include and/or be able to detect other sources, such as electromagnetic radiation, sound, or other types of waves, instead of or in addition to light.

Optionally, the apparatus of the present teachings may also include an intermediate work-piece support platform. The intermediate work-piece support platform may include a support surface that can be actuated to raise or lower a steering column assembly placed thereon. For example, the intermediate work-piece support platform may be adapted to be raised or lowered (e.g., pneumatically, via one or more air cylinders that support an upper surface, by an electric motor, or otherwise). The intermediate work-piece support platform may have an upper surface that includes a concave depression, a v-shaped depression or some other depression adapted to support an intermediate portion of the steering column assembly (e.g., between the first and second ends) so that the first end of the steering column assembly can be brought in generally opposing relationship with the drive sleeve (e.g., their respective longitudinal axes are generally aligned). For example, the intermediate work-piece support platform may receive a steering column assembly at a first height. It may then be actuated to raise the steering column assembly to a second height so that the longitudinal axis of the steering column assembly is generally opposite the longitudinal axis of the drive sleeve. Thereafter, upon engagement of the first end of the steering column assembly with the drive sleeve, the intermediate work-piece support platform is lowered so that it no longer supports the steering column assembly.

The apparatus of the present teachings optionally may also include a suitable marking device adapted for marking a visual indicator onto a surface of a steering column assembly that has been inspected based upon the results of the inspection. For example, if a steering column assembly fails an inspection the marking device may be actuated to mark the steering column assembly. Alternatively, if a steering column assembly passes an inspection the marking device may be actuated to mark the steering column assembly. The marking device may include a coating spray device that includes a spray nozzle that is in fluid communication with a source of a liquid coating (e.g., a dye, a colorant, or some other coating) aimed toward a steering column assembly while the steering column assembly is positioned on the apparatus of the present teachings For example, a suitable bracket may be mounted to the headstock for carrying the spray nozzle in opposing relation to an open first end of the drive sleeve.

The apparatus may also be part of an assembly that includes a housing. The housing may be a substantially enclosed housing. The apparatus, the housing, or both, may have an associated display device for providing an operator with visual results from an inspection. There may be one or more suitable input devices for allowing an operator to control operation of the machine. There may be one or more bins for collection of steering assemblies that pass or fail inspection. There may be one or more load cells associated with the collection bins apparatus that is in electronic signaling communication with a processor that identifies if a steering column assembly passes or fails an inspection. In this manner the load cell can assure that a steering column assembly that passes or fails an inspection is placed in the proper collection bin. There may be other suitable hardware to assure that an operator has properly segregated inspected steering column assemblies to separate the failed from the passed assemblies. The apparatus may include a device that optically analyzes whether a coating has been applied to a steering column assembly.

As can be appreciated from the above, use of the apparatus of the present teachings may include the general steps of supportingly locating a steering column assembly on the apparatus so that the first end portion of the steering column assembly can become engaged by the drive sleeve. A step may include advancing the drive sleeve (e.g., by driving the headstock) toward the first end portion of the steering column assembly until the first end portion of the steering column assembly becomes engaged by the drive sleeve. Optionally, the drive sleeve is advanced (e.g., via longitudinally translating the headstock) until any telescopic extension of the steering column assembly that may exist is eliminated. The drive sleeve also may be advanced (e.g., via longitudinally translating the headstock) so that the second end of the steering column assembly contacts the roller pin of the tailstock. Upon contacting the roller pin there may be a step of elevating the second end by bearing against the second end until the roller pin becomes engaged in a recess formed in the second end of the steering column assembly. Thereafter, a step of rotating the steering column assembly about its longitudinal axis may be performed, such as by rotatably driving the drive sleeve about its longitudinal axis. While the steering column assembly is rotated about its longitudinal axis, a surface feature of interest is optically analyzed. For example, a step of optically scanning a feature of interest (e.g., a surface feature of interest) may be performed. The optical scanning may be to analyze a feature of interest selected from dimple location, dimple depth, dimple location relative to a groove in the spline shaft portion, sensor sleeve appearance, sensor sleeve runout, sensor sleeve peripheral crimp appearance, sensor sleeve crimp angle, distance from a location on the sensor sleeve to a shoulder on the spline shaft portion, location of a c-ring groove, distance of a c-ring groove relative to a surface on the worm-wheel, position of the sensor sleeve relative to a worm-wheel surface, distance from a location on the sensor sleeve to a worm-wheel surface, location of the worm-wheel relative to a predetermined location in the spline shaft portion, or any combination of the foregoing.

A step may be performed of comparing data obtained from the scanning with a known reference value. For example, a step may be performed of scanning a steering column assembly that satisfies predetermined desired quality criteria. Data obtained from such scanning may be stored and used in the comparing step. One approach to the comparing step involves comparing relative positions of surface features of interest with predetermined values for relative positions, without regard to measurements of dimensions. Based upon the results of the inspecting, there may be one or more steps of segregating steering column assemblies that pass inspection from those that fail inspection. The segregating may include locating one or more steering column assemblies in a collection bin. There may be one or more steps of applying a coating onto a steering column assembly that passes or fails an inspection. There may be one or more steps of analyzing (e.g., optically) whether a steering column assembly has a coating applied thereto prior to installation of the steering column assembly in a vehicle.

The teachings herein are described by reference to a particular illustrative steering column assembly. In general, such an illustrative steering column assembly may have a longitudinal axis, a first end adapted to be attached to a steering wheel, a first end portion adjoining the first end and extending partially along the longitudinal axis, a second end (which may have a recess formed therein, a projection extending therefrom, or both) and a second end portion. At the first end portion there may be at least one telescopic shaft subassembly, such as an outer steering wheel interface shaft tube that has a steering wheel interface (at the first enc of the steering column assembly) and that may have a suitable tube in tube surface arrangement. It may have two or more tubes having generally smooth opposing surfaces slidable relative to each other For example, it may have a tube in tube arrangement by which a plurality of longitudinal extending ribs on an inner wall of an outer tube slidingly engage an inner splined shaft having an outer longitudinal spline surface. Mounted to the second end portion may be a worm-wheel having a forward and a rearward face. The second end portion may include a worm-wheel stub shaft, which may include one or more grooves adapted to receive a snap ring The stub shaft may be coupled at one end with an intermediate shaft (which, in turn may be coupled with a steering rack and pinion assembly) by way of a suitable coupling. The stub shaft may be coupled from its opposing end with the inner shaft (e.g., the inner splined shaft). For example, the stub shaft may be coupled by way of a torsion bar that is mounted at one of its ends generally within an end portion of the inner shaft (e.g., the inner splined shaft) and is mounted at its other end the stub shaft.

Adjoining the worm-wheel, and being carried on the inner shaft (e.g., the inner splined shaft), there may be a suitable sensor sleeve. The sensor sleeve may be part of a sensor assembly adapted for detecting torque (e.g., by impedance detection, by inductance detection (such as is taught in U.S. Pat. No. 7,814,803, incorporated by reference), by magnetic detection (such as is taught in U.S. Pat. No. 8,102,138, incorporated by reference), or otherwise) of the worm-wheel stub shaft relative to the inner shaft (e.g., the inner splined shaft). In this manner, it may be possible to detect when one or more predetermined torsional conditions are satisfied for causing a power assist device (e.g., a power assist motor) to supply additional force to the worm-wheel stub shaft for assisting a vehicle operator complete a steering operation. For instance, the sensor sleeve may include a first end and a second end, such that the second end substantially adjoins a shoulder formed on the rearward face of the worm-wheel. The sensor sleeve may include a plurality of windows circumferentially disposed about the sleeve. The sensor sleeve may generally surround one or more bodies associated with the stub shaft in a sensing relationship, so that when there is torsional movement of the inner shaft (e.g., the inner splined shaft) causing the sleeve to rotate relative to the one or more bodies, and there is not a corresponding torsional response by the worm wheel stub shaft, the torque generated by the inner shaft (e.g the inner splined shaft) is detected and the power assist device is actuated.

To help assure proper alignment of components for operation of the sensor assembly, the first end of the sensor sleeve may include a suitable crimp for maintaining its portion on the inner shaft (e.g. the inner spline shaft). For example, it may have a peripheral crimp that extends substantially the entirety of the periphery of the first end of the sleeve and engages an outer surface of the inner shaft (e.g., the inner spline shaft), so that the sleeve resists longitudinal movement relative to the inner shaft (e.g., the inner spline shaft). The crimp may have an angle ($\alpha_c$, see FIG. 1B) relative to the longitudinal axis. For example, the crimp may have an angle that ranges from about 10 to about 30°, such as about 14 to about 22°. The sensor sleeve may also be secured relative to the inner shaft (e.g., the inner spline shaft) with a dimple or other plastic deformity in order to help resist torsional movement of the sensor sleeve relative to the inner shaft (e.g., the inner spline shaft). The dimple or other deformity may have a depth relative to an outer surface of the sleeve. For example, the dimple may have a depth ranging from about 0.2 mm to about 0.8 mm (e.g., about 0.4 to about 0.6 mm). The dimple may penetrate into an opposing recess (e.g., a longitudinal groove) formed on the inner shaft (e.g., the inner splined shaft).

As will be appreciated, other components may form part of the steering column assembly, such as a gear box, an electric power assist motor, a worm-wheel housing unit, one or more control units, one or more vehicle attachment brackets, one or more bearings. etc. An example of an assembly that may be made in accordance with the present teachings is provided, without limitation, in U.S. Pat. No. 8,102,138, incorporated by reference for all purposes.

In accordance with the teachings herein, it is envisioned that an apparatus of the present teachings will be employed in one or more steps of inspecting the crimp (e.g., for location, for peripheral continuity, for angle, or any combination thereof), inspecting the dimple (e.g., for location, depth or, or both), inspecting the worm-wheel position relative to one or more other components of the steering column assembly, inspecting the sensor sleeve for any surface defect, inspecting the relative position of a face of the worm-wheel and a back shoulder on an inner shaft (e.g the inner splined shaft) of the steering column assembly, inspecting an interface between the worm-wheel and a worm-wheel stub shaft of the steering column assembly (e.g., to help assure rotational imbalance is avoided), at any combination thereof. It should be recognized, however, that the teachings are not intended to be limited to such assembly. The use of the apparatus and method herein is contemplated for other steering column assemblies as well.

As will also be seen, though the teachings herein are illustrated by reference to a particular illustrative steering column assembly having a first steering wheel interface, the components of the apparatus of the present teachings make it suitable for essentially universal application over a range of different steering column assemblies, each having a different steering wheel interface. For example, the teachings make it possible to employ the apparatus for various steering wheel interfaces that may differ relative to each other in length diameter, tube and/or shaft geometry, or otherwise.

In general, the teachings herein envision a method of non contact inspection of a steering column assembly. The method may include a step of engaging a first end portion of the steering column assembly in a drive sleeve. The method may employ a step of translating the steering column assembly so that the second end of the assembly bears against a roller pin and is brought into axial alignment with the longitudinal axis of tie roller pin, which step may include elevating or otherwise transversely translating the second end of the steering column assembly from a first position to a second position. The method may include a step of elevating or otherwise transversely translating the steering column assembly from a first position to a second position at a location that is intermediate the first end and the second end of the assembly. The method may include a step of rotating the steering column assembly while scanning the assembly.

During the rotating step, data may be obtained continuously about the periphery of a region of interest, data may be obtained intermittently about the periphery of the region of interest, or both. For example, a plurality of scans may be made (e.g., 5 or more, 10 or more, 20 or more, 30 or more, 40 or more, 360 or less, 180 or less, 90 or less, or otherwise) at predetermined intervals for each revolution of the steering column assembly about its longitudinal axis. One or a plurality of revolutions may be made about the longitudinal axis for performing an inspection.

Such a step may include gathering data about feature of interest from the scan and comparing such data with predetermined reference data. For example, predetermined reference data may be obtained by scanning a part having features of interest known to satisfy predetermined quality criteria. Such data may be stored in memory and recalled for use when performing a comparing step. It is possible that the reference data will include: relative positions of two or more surface features, one or more dimensions associated with one or more surface features, a surface topography for one or more surface features, or any combination thereof. In one approach it is envisioned that the comparing step compares only relative positions of two or more surface features as between those of a known reference part and those of an assembly being inspected. That is, a qualitative comparison is made of the surface features without regard to any quantitative data about the feature. There may be a step of applying an optically detectable coating (e.g., a paint, a dye, or otherwise) to a steering column assembly to denote whether or not the assembly has passed an inspection.

The method may include a step of issuing an alarm signal (e.g., an audible and/or visual signal) if a steering column, assembly being inspected fails to meet certain criteria, or alternatively, issuing an alarm signal (e.g., an audible and/or visual signal) if a steering column meets certain criteria. For example, there may be a step of optically analyzing (e.g., using an automated optical scanning device) if an optically detectable coating has been applied, and thereafter issuing an alarm signal based upon the result of the step of optically analyzing.

Based upon the presence or absence of an alarm signal, an operator may place a steering column assembly into a collection bin. For example, there may be a collection bin for a steering column assembly that passes an inspection, a collection bin for a steering column assembly that fails an inspection, or both. There may be a step of sensing (e.g., using a load sensor, a motion sensor, or otherwise) whether an operator has placed a steering column assembly into a collection bin as directed.

One or more other steps may be employed, such as for controlling operation of the apparatus of the present teachings. For example, there may be one or more security steps employed to assure only authorized operators use the apparatus. For example, there may be a step of detecting data about an operators fingerprint and comparing it against data about fingerprints of authorized operators stored in memory.

Figure 4A:
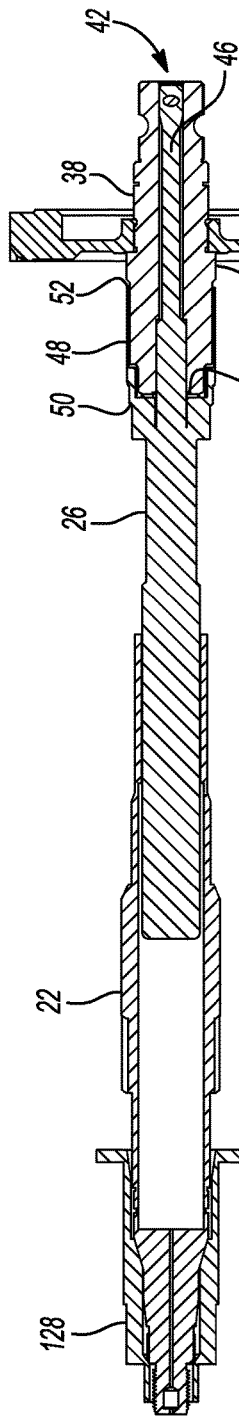
FIGS. 4A, 4B, 4C and 4D are a series of side sectional views illustrating the versatility of the drive sleeve of FIGS. 3A and 3B to accommodate a number of different shafts.
Figure 4B:
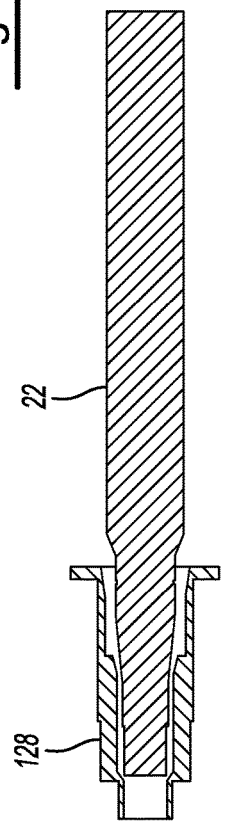
Figure 4C:
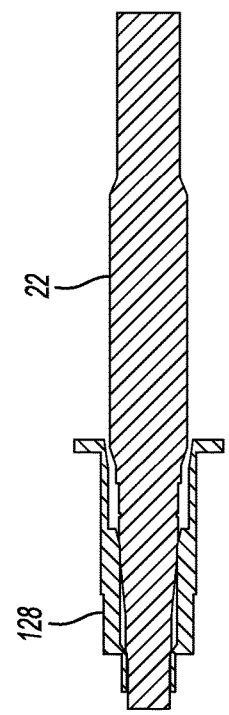
Figure 4D:
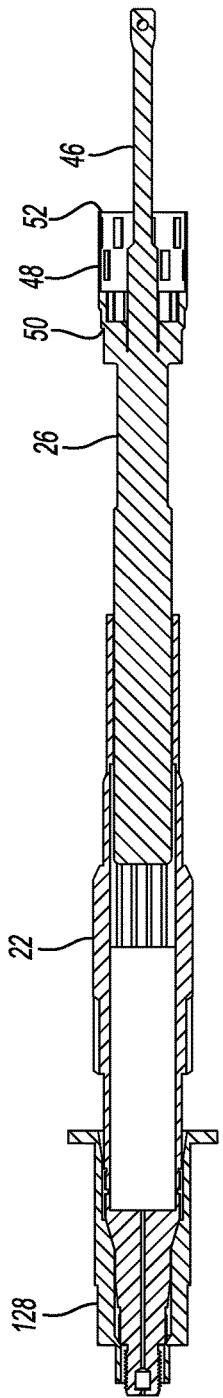

Referring now to FIGS. 1A, 1B, 4A, 4D, 5A and 5D, there is seen an illustrative steering column assembly 10 for which an inspection can be performed in accordance with the present teachings. In general, the assembly 10 has a longitudinal axis (LA), a first end 12 adapted to be attached to a steering wheel (not shown), a first end portion 14 adjoining the first end and extending partially along the longitudinal axis, a second end 16 and a second end portion 18. At the first end portion 14 there may be at least one telescopic shaft subassembly 20, such as an outer steering wheel interface shaft tube 22 that has an associated steering wheel interface 24 and that has a plurality of longitudinal extending ribs on an inner wall that slidingly engage an inner shaft 26 (shown as an inner splined shaft having an outer longitudinal spline surface portion 28 and a forward end portion 30). Mounted to the second end portion 18 may be a worm-wheel 32 having a forward face 34 and a rearward face 36. The second end portion includes a worm-wheel stub shaft 38, which may include one or more grooves 40 adapted to receive snap ring. The stub shaft 38 may be coupled proximate a stub shaft forward end portion 42 with an intermediate shaft by way of a suitable coupling (not shown). The stub shaft 38 may be coupled from its opposing end 44 (shown in FIG. 4A) with the inner splined shaft (e.g., by way of a torsion bar 46, as depicted in FIG. 4A) that is mounted at one of its ends generally within the forward end portion of the inner shaft 26 and is mounted at its other end to the stub shaft.

Adjoining the worm-wheel 32, and being carried on the inner shaft 26, there is a suitable sensor sleeve 48. The sensor sleeve 48 has a first end 50 and a second end 52, such that the second end 52 substantially adjoins a shoulder 54 (shown in FIGS. 4A and 5A) formed on the stub shaft proximate the worm-wheel 32. The sensor sleeve 48 has a plurality of windows 56 circumferentially disposed about the sleeve. At the first end 50 of the sensor sleeve there is a crimp 58. The crimp may have an angle $\alpha_c$. The crimp may have a width $1_c$. A dimple 60 is formed in the sensor sleeve as well, which penetrates into a groove 62 of the inner shaft 26. The sensor sleeve may generally surround one or more bodies (not shown) associated with the stub shaft in a sensing relationship, so that when there is torsional movement of the inner shaft causing the sleeve to rotate relative to the one or more bodies, and there is not a corresponding torsional response by the worm-wheel stub shaft, the torque generated by the inner splined shaft is detected and the power assist device is actuated.

At the second end 16 of the steering column assembly there may be a recess 64, which desirably is located in the center of the second end.

The teachings herein envision inspection of one or any combination of the features of the crimp 58, the dimple 60, the groove 62, the relative positions of one or more of the features of the assembly 10. Without limitation, for example, the scanning can be performed to analyze dimple location, dimple depth, dimple location relative to a groove in the spline shaft portion, sensor sleeve appearance, sensor sleeve runout, sensor sleeve peripheral crimp appearance, sensor sleeve crimp angle, distance from a location on the sensor sleeve to a shoulder on the spline shaft portion, location of a c-ring groove, distance of a c-ring groove relative to a surface on the worm-wheel, position of the sensor sleeve relative to a worm-wheel surface, distance from a location on the sensor sleeve to a worm-wheel surface, location of the worm-wheel relative to a predetermined location in the spline shaft portion, or any combination of the foregoing.

With reference to FIGS. 2A-2G, there is seen how an illustrative steering column assembly, such as the assembly 10, is inspected using an apparatus 110 of the present teachings.

The apparatus 110 includes at least one support structure 112 having a longitudinal axis (LA2). A headstock 114 is translatably mounted on the at least one support structure 112 and includes at least one work-piece drive motor 114a. The motor is adapted to rotate a steering column assembly that is loaded in the apparatus about the longitudinal axis of the steering column assembly. The headstock 114 includes a shroud 116. The shroud may substantially surround the headstock 114, but may include openings 118 at opposing ends. In that way, the headstock will be able to receive the first end portion 14 of the steering column assembly 10 and will also expose the first end so that the end is able to be coated with a colorant, dye or other detectable coating that denotes whether or not the steering column assembly 10 has passed inspection. The shroud is configured to include guide structures 120 adapted to translate along one or more longitudinally oriented tracks 122 on the underside of the support structure. The headstock may otherwise be adapted to be driven relative to the at least one support structure via a linear actuator 124 driven by a suitable motor 126, which may be mounted on the underside of the support structure 112.

A drive sleeve 128 having a longitudinal axis (LA3) is supported in the headstock 114 for rotation by the work-piece drive motor 114a. The work-piece drive motor 114a is illustrated as including an output drive mechanism (e.g., a shaft that supports a gear or a roller) 116a that operatively engages an opposing drive mechanism 116b (e.g., a gear or a roller) that surrounds the drive sleeve 128 (which may itself be supported by a suitable bearing). Thus, the work-piece drive motor may rotate for causing a steering column assembly that is supported in the drive sleeve to rotate about the longitudinal axis of the steering column assembly. For example, the drive sleeve may be surrounded along a portion of its length by a suitable bearing. The drive sleeve may have a suitable gear 128a that generally surrounds the sleeve and is driven by a gear associated with the output shaft of the work-piece drive motor or an intermediate idler gear 116b.

Figure 3A:
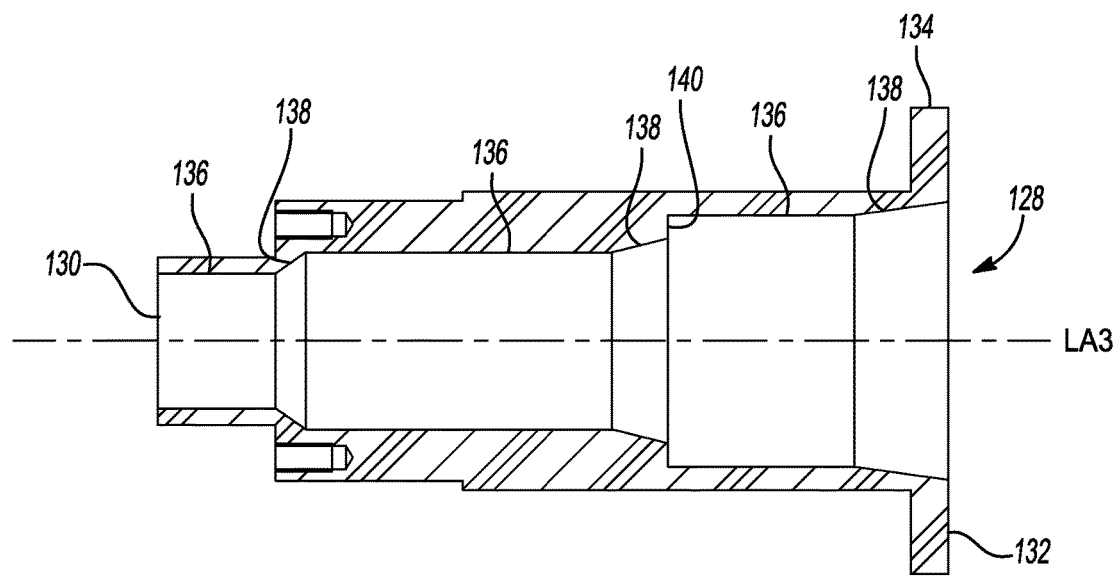
FIG. 3A is a side sectional view of a motor driven rotatable end region support structure and drive sleeve of the apparatus of FIG. 2A, in accordance with one illustrative example of the present teachings.
Figure 3B:
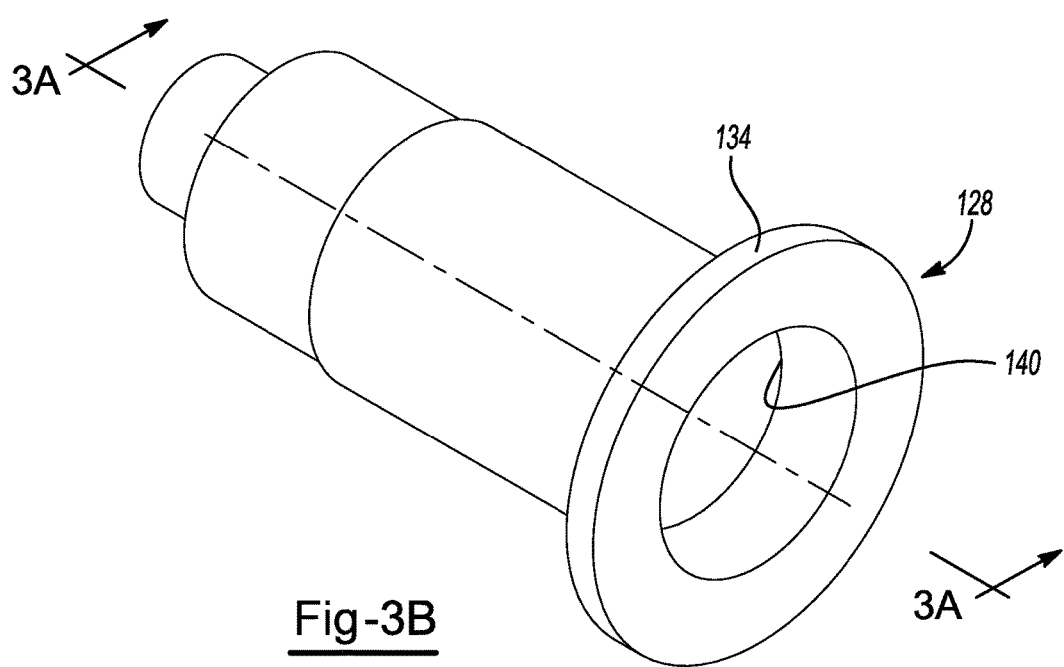
FIG. 3B is a perspective view of the drive sleeve of FIG. 3A.

The drive sleeve longitudinal axis is generally parallel with (or coaxial with) the longitudinal axis of the steering column assembly that it receives, a first end and a second end. As seen in FIG. 3A, at the first end of the drive sleeve 128, there is an opening 130, so that a through passage is defined along the length of the drive sleeve. At the second end 132 there is a peripheral flange 134. The drive sleeve has an inner wall surface that is adapted for receiving and engaging the first end portion of the steering column assembly. The inner wall surface is illustrated to include cylindrical wall segments 136, and frusto-conical wall segments 138. The segments progressively reduce in size from the second end toward the first end, for at least a portion of the length of the drive sleeve. One or more shoulders 140 may be defined at the intersection of successive wall segments. As a result of having such inner wall structure, the drive sleeve is able to receive the first end portion of a variety of different steering column assemblies, each having a differently configured and/or differently dimensioned first end portion. This is seen, by way of example, in the drawings of FIGS. 4A-4D and 5A-5D, discussed herein. The shoulders allow such steering column assemblies to engage the drive sleeve at a location along the first end portion. For examples a shoulder may engage a tapered wall of an outer tube of the steering column assembly (e.g., an outer tube of a telescopic steering column assembly).

Figure 7A:
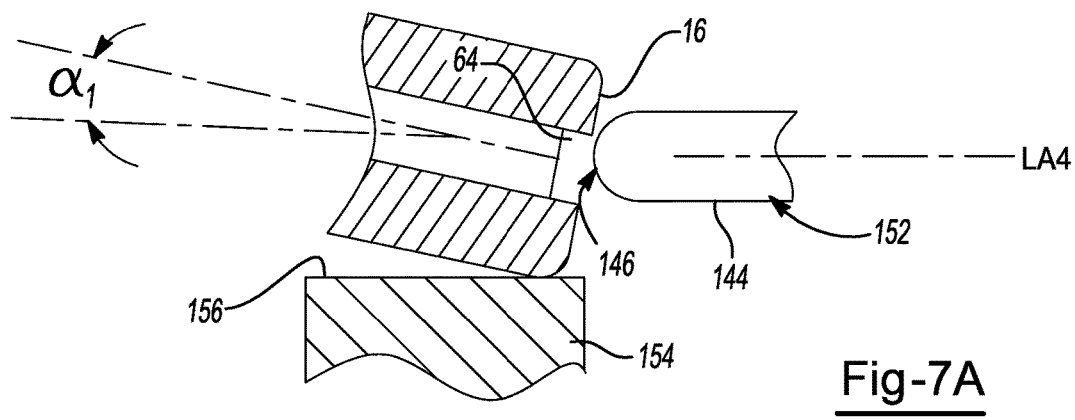
FIGS. 7A, 7B and 7C are side sectional views showing how a roller pin is employed for elevating a steering column assembly and suspending it for inspection.
Figure 7B:
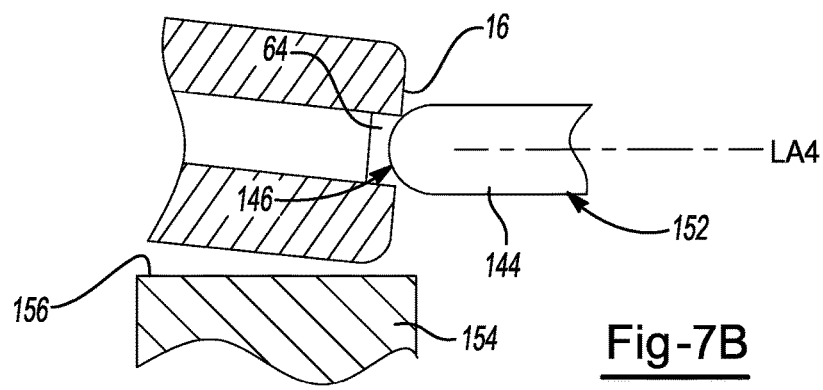
Figure 7C:
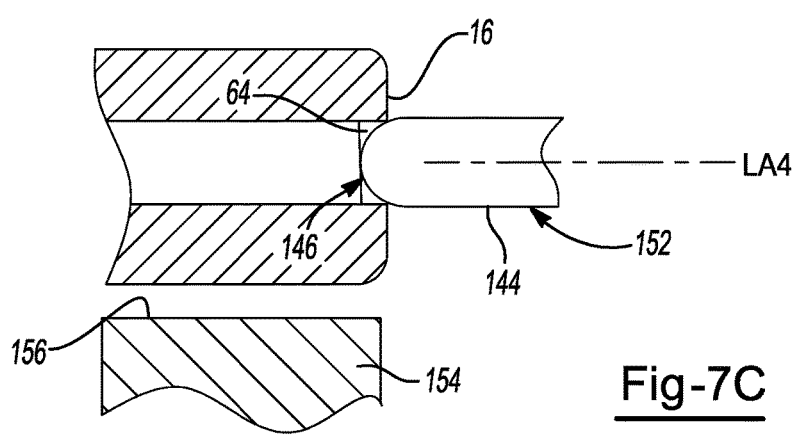

A tailstock 142 (which may be carried on the support structure or on another support structure) carries a suitable roller pin 144, e.g., an idler pin, having a longitudinal axis (LA4). The longitudinal axis of the roller pin is substantially juxtaposed with the longitudinal axis (LA3) of the drive sleeve. The roller pin has an outer surface that is adapted for engaging the second end portion of the steering column assembly and for bearing against the second end of the steering column assembly during rotation of the shaft so that the shaft is suspended relative to the at least one support structure. The roller pin may include a free end portion 146 that engages the second end of a steering column assembly being inspected, As seen in FIGS. 2H, 2J, and FIGS. 7A-7C, the free end 146 of the roller pin may be dimensioned and/or shaped so that it can penetrate into the recess 64 at the second end 16 of the steering column assembly. For instance, the free end 146 may have a rounded tip (as illustrated in FIGS. 7A-7C) or a conical tip 148 and a tapered portion 150 that is disposed on a supported rod portion 152 (which may have a threaded portion for attachment to a bearing component). The supported rod, the tip 148 or both may be adapted for rotation For instance, it may be rotatably supported by a suitable bearing assembly 153 (which is depicted to include a round bearing supported by a bearing block) associated with the tailstock 142. The roller pin thus may remain in a fixed longitudinal position, but may be adapted for rotation about a longitudinal axis.

A work-piece end support platform 154 is shown as located next to the tailstock 142. The work-piece end support platform 154 is fixed at a predetermined height, relative to the support structure 112 so that at least a portion of the end of the stub shaft that is disposed thereon is generally juxtaposed with the free end 146 of the roller pin. The work-piece end support platform 154 has an upper surface 156 adapted to support the second end portion of a steering column assembly when the steering column assembly is initially placed for inspection on the apparatus.

With reference more particularly to FIGS. 7A-7C, the upper surface 156 is located at a position that is offset relative to the longitudinal axis of the roller pin. The upper surface may be located at a position such that when the second end portion of a steering column assembly is initially placed thereon, and the first end portion becomes engaged by the drive sleeve, the longitudinal axis of the steering column assembly is initially at an angle ($\alpha_1$; see FIG. 7A). As discussed, the angle ($\alpha_1$) may be about 1 to about 20°, and more preferably about 2 to about 10° relative to the longitudinal axis of the drive sleeve. As seen from FIGS. 7A-7C, as the headstock is translated toward the tailstock, the second end of the steering column assembly will contact the roller pin and bear against the roller pin 144 until the roller pin becomes located within the recess 64 of the second end 16. As a result, the second end will become elevated from the upper surface of the work-piece end support platform.

With reference again to FIGS. 2A-2C and 2D-2G, there are depicted a plurality of optical scanning devices, namely first, second, and third optical scanning devices 160a, 160b and 16c (in this example, there are three optical devices). In this illustration, the optical scanning devices are each supported in spaced relation from the support structure 112 (by one or more bracket structures 162) The optical scanning devices are positioned so that its emitted beam is aimed at various regions of interest of the supported steering column assembly, and reflection of the beam is able to be detected by a detector associated with the beam emitter. In the example shown in FIGS. 2A-2G, the first optical scanning device 160a is positioned so that its emitted beam is aimed generally at the region proximate the forward face of the worm-wheel, so that the worm wheel position relative to the stub shaft can be inspected and analyzed. The second optical scanning device 160b is positioned so that its emitted beam is aimed generally at the region proximate the sensor sleeve so that the crimp 58, the dimple 60, the groove 62 or any combination thereof can be inspected and analyzed. The third optical scanning device 160c is positioned so that its emitted beam is aimed generally at a shoulder 26a on the shaft 26, the end 50 of the sleeve 48, or both (see FIG. 1A), so that (for instance) the relative position of the sleeve 48 and shoulder 26a can be inspected and analyzed.

In the illustrated embodiment, the apparatus 110 also includes an intermediate work-piece support platform 164. The intermediate work-piece support platform 164 includes a support surface 166, which has a generally v-shaped depression that can be actuated to raise or lower a steering column assembly placed thereon. In this manner, a steering column assembly can be positioned on the support surface and raised or lowered (e.g., via one or more air cylinders 167 (see FIG. 2I)) to be brought in generally opposing relationship with the drive sleeve (e.g., their respective longitudinal axes are generally aligned). After engagement by the drive sleeve, with the first end portion of the steering column assembly the intermediate work-piece support platform 164 can be lowered so that it no longer supports the steering column assembly 10.

The illustrative apparatus 110 of FIGS. 2A-2G is depicted to include an optional marking device 168 adapted for marking a visual indicator onto a surface of a steering column assembly that has been inspected based upon the results of the inspection. The marking device 168 has a spray nozzle 170 that is in fluid communication with a source of a liquid coating (e.g., a dye, a colorant, or some other coating) aimed toward a steering column assembly while the steering column assembly is positioned on the apparatus of the present teachings. In the embodiment shown, a bracket 172 is mounted to the headstock 114 for carrying the spray nozzle 170 in opposing relation to the opening 130 in the drive sleeve (see FIG. 3A).

Figure 6B:
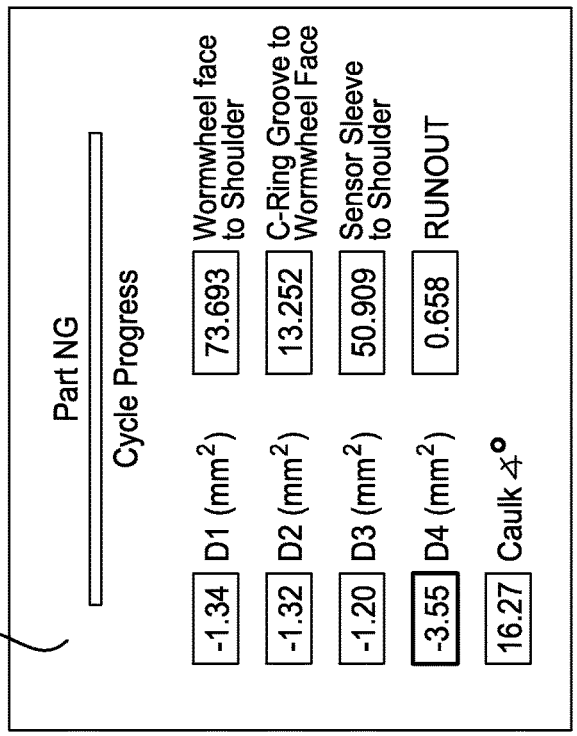
FIG. 6B is a depiction to illustrate data displayed in accordance with the teachings.
Figure 6A:
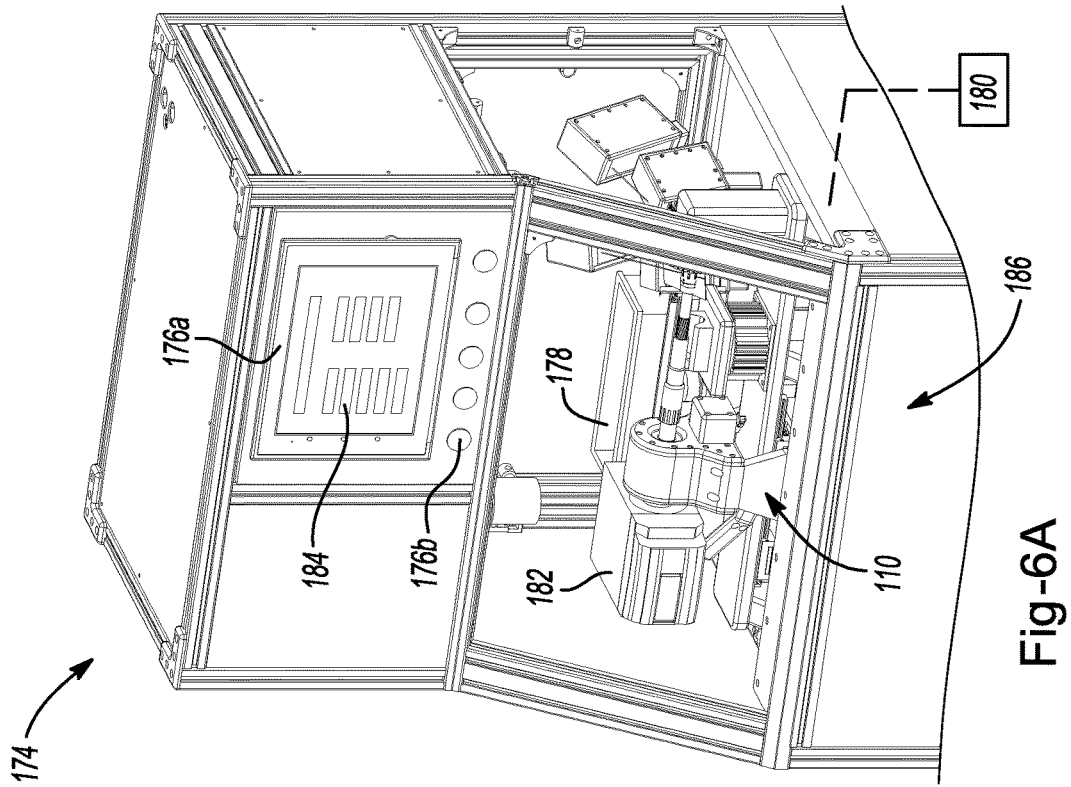
FIG. 6A is a depiction of an illustrative system in accordance with the present teachings, including an apparatus contained within a housing.

With reference to FIG. 6A, there is depicted how the apparatus 110 may also be part of an assembly 186 that includes a housing 174 with an associated display device 176*a* for providing an operator with visual results from an inspection. One or more suitable input devices 176*b* (e.g., switches) for allowing an operator to control operation of the machine are shown. A bin 178 for collection of one or more steering assemblies that pass or fail inspection may be within the housing, or proximate the housing and exterior of the housing. There may be one or more load cells 180 associated with a collection bin. There may also be a suitable optical detector 182 (inside or outside of the housing) for analyzing whether a coating has been applied to a steering column assembly. One or more data output displays 184 may provide visual output that indicates whether a steering column assembly that has been inspected has passed or failed and/or what parameters have or have not been satisfied by the inspected assembly. FIG. 6B illustrates an example of illustrative data that may be output via one or more data output displays 184. In that illustration, measure distances between certain surface features are provided as well as caulk crimp) angle. For the D4, it is shown as highlighted due to an abnormal deviation from the reference distance for the runout of the sensor sleeve relative to the shoulder 26*a*, Other distances are shown as meeting acceptable tolerances. With reference to FIG. 1A, the measured distances D1 (worm-wheel face to shoulder 26*a*), D2 (C-ring groove 40 to worm-wheel face), D3 (sensor sleeve to shoulder 26*a*) and D4 (runout of sensor sleeve along shaft 26) are shown.

As discussed previously, the teachings herein envision scanning to assure that a steering column assembly being inspected meets certain predetermined criteria. Without limitation, for example, the scanning can be performed to analyze dimple location, dimple depth, dimple location relative to a groove in the spline shaft portion, sensor sleeve appearance, sensor sleeve runout, sensor sleeve peripheral crimp appearance, sensor sleeve crimp angle, distance from a location on the sensor sleeve to a shoulder on the spline shaft portion, location of a c-ring groove, distance of a c-ring groove relative to a surface on the worm-wheel, position of the sensor sleeve relative to a worm-wheel surface, distance from a location on the sensor sleeve to a worm-wheel surface, location of the worm-wheel relative to a predetermined location in the spline shaft portion, or any combination of the foregoing.

In regards to the operation of the illustrated embodiment, as can be appreciated, upon being placed on the intermediate work-piece support platform 164, the steering column assembly 10 is caused to be raised or lowered while on the platform so that the first end is generally aligned with the drive sleeve 128. The headstock 114 is actuated to translate the drive sleeve so that the drive sleeve engages the first end portion 14 of the steering column assembly, and to cause the second end 16 of the steering column assembly to bear against the roller pin 144, and elevate the second end portion 18 from the work-piece end support platform 154. The intermediate work-piece support platform may then be retracted as well so that the steering column assembly is suspended by the drive sleeve 128 and the roller pin.

The work-piece drive motor 114*a* causes the drive sleeve to rotate about its longitudinal axis, while the optical scanning devices 160*a*, 160*b* and 160*c* scan the regions of the steering column assembly to which they are aimed, and obtain surface feature data for the regions. Surface feature data obtained by the optical scanning devices is compared against reference data for determining whether the surface features of interest satisfy predetermined criteria.

As with any of the embodiments herein, data may be obtained continuously about the periphery of a region of interest. Data may be obtained intermittently about the periphery of the region of interest. For example, a plurality of scans may be made (e.g., 5 or more, 10 or more, 20 or more, 30 or more, 40 or more, 360 or less, 180 or less, 90 or less, or otherwise) at predetermined intervals for each revolution of the steering column assembly about its longitudinal axis.

As can be appreciated from the above, use of the illustrated apparatus 110 of the present teachings may include the general steps of supportingly locating a steering column assembly 10 as depicted in FIG. 1A on the apparatus 110 so that the first end portion 14 of the steering column assembly 10 can become engaged by the drive sleeve 128. A step may be employed of advancing the drive sleeve 128 (e.g., by driving the headstock 114) toward the first end portion 14 of the steering column assembly 10 until the first end portion 14 of the steering column assembly 10 becomes engaged about its periphery by the drive sleeve (e.g., at a shoulder 140 of the drive sleeve). The first end 12 of the steering column assembly may penetrate through the opening 130 of the drive sleeve or may be exposed through the opening 130. A step may be employed of advancing the drive sleeve 128 (e.g., via longitudinally translating the headstock and its associated shroud) so that the second end 18 of the steering column assembly 10 contacts the tip 148 of the free end 148 of the roller pin 144. Upon contacting the roller pin there may be a step of elevating the second end by bearing against the second end 16 until the roller pin 144 becomes engaged in the recess 64 formed in the second end 16 of the steering column assembly 10. Thereafter, a step of rotating the steering column assembly 10 about its longitudinal axis may be performed, such as by rotatably driving the drive sleeve 128 about its longitudinal axis. While the steering column assembly is rotated about its longitudinal axis, a surface feature of interest is optically analyzed. For example, a step of optically scanning a surface feature of interest (e.g., the dimple 60, the relationship of the dimple 60 to the inner shaft groove 62, the crimp location, the crimp 58 angle, the relative position of the sensor sleeve 48 relative to a feature of the steering column assembly (e.g., relative to the stub shaft shoulder 54), surface topography of the sensor sleeve 48, the interface between the worm-wheel 32 and the shaft on which it is mounted, the relative position of the worm-wheel and a surface feature of interest, or other surface profile, or any combination thereof), may be performed. A step may be performed of comparing data obtained from the scanning with a known reference value. For example, a step may be performed of scanning a steering column assembly that satisfies predetermined desired quality criteria. Data obtained from such scanning may be stored and used in the comparing step. One approach to the comparing step involves comparing relative positions of surface features of interest with predetermined values for relative positions, without regard to measurements of dimensions. Based upon the results of the inspecting, there may be one or more steps of segregating steering column assemblies that pass inspection from those that fail inspection. The segregating may include locating one or more steering column assemblies in a collection bin. There may be one or more steps of applying a coating onto a steering column assembly that passes or fails an inspection. For example, the spray nozzle 170 may dispense a coating of a dye or other detectable coating onto the first end of the steering column assembly that is exposed within the opening 130. There may be one or more steps of analyzing (e.g., optically) whether a steering column assembly has a coating applied thereto prior to installation of the steering column assembly in a vehicle. For instance, a step of scanning the steering column assembly may be performed using the optical detector 182. Based upon the scanning step, a step of indicating whether the coating is applied may be employed. For instance the readout device 184 may display a result and/or display an instruction to the operator. By way of illustration, without limitation, the readout display may issue a read-out that instructs an operator to load a faulty steering column assembly into the collection bin 178. A step of sensing whether the steering column assembly has been loaded in the bin may be performed, such as by the load cell 180. If the steering wheel assembly has not been loaded, the apparatus may temporarily cease operation until such loading has occurred. There may also be a step of assuring that steering column assemblies loaded into the bin are not removed except by predetermined operators, such as an operator that has entered a suitable security code, or has satisfied some other security criteria.

As seen from the above, the general teachings herein find suitable application for the inspection of one or more stakes, crimps, dimples, or other plastic deformity for joining a tube in tube, and/or a shaft in tube structure.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

As can be appreciated, variations in the above teachings may be employed. For example, it may be possible to employ one or more motors for rotating the steering column assembly at or near its second end and/or at some intermediate location.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature. pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination The use of the terms "comprising" or "including" to describe combinations of elements, ingredients, components or steps herein also contemplates embodiments that consist essentially of, or even consisting of, the elements, ingredients, components or steps.

Plural elements, ingredients, components or steps can be provided by a single integrated element, ingredient, component or step Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

Relative positional relationships of elements depicted in the drawings are part of the teachings herein, even if not verbally described. Further, geometries shown in the drawings (though not intended to be limiting) are also within the scope of the teachings, even if not verbally described.

What is claimed is:

1. An apparatus for inspecting a steering column assembly having a first end portion, a second end portion and a longitudinal axis, comprising:
  a. at least one support structure having a longitudinal axis;
  b. a headstock mounted on the at least one support structure and including at least one work-piece drive motor;
  c. a drive sleeve having a longitudinal axis, the drive sleeve being supported in the headstock for rotation by the at least one work-piece drive motor and including an inner wall surface that is adapted for receiving and engaging the first end portion of the steering column assembly;
  d. an optional tailstock adapted to engage the second end portion of the steering column assembly and which optionally includes a roller pin; and
  e. at least one optical scanning device adapted to optically scan a feature of interest of the steering column assembly while the steering column assembly is rotated about its longitudinal axis for gathering data for identifying one or more deviations from one or more predetermined values for the feature of interest; wherein the at least one optical scanning device emits a light beam and the at least one optical scanning device is oriented so that the light beam is aimed at the feature of interest of the steering column assembly and reflected light of the light beam off the feature of interest can be detected by the at least one optical scanning device; wherein, upon receiving and engaging the first end portion of the steering column assembly, the at least one work-piece drive motor operates to rotate the drive sleeve to thereby rotate the steering column assembly so that the steering column assembly can be scanned by the at least one optical scanning device; and f. a nozzle adapted to spray a colorant onto the steering column assembly based upon data obtained from the at least one optical scanning device; wherein the nozzle is disposed generally opposite the first end portion of the steering column assembly and is adapted for spraying colorant onto the first end portion of the steering column assembly.

2. The apparatus of claim 1, wherein the headstock is adapted to translate relative to the at least one support structure generally along the longitudinal axis of the at least one support structure;

wherein the apparatus includes a tailstock that carries a roller pin having a longitudinal axis that is substantially juxtaposed with the longitudinal axis of the drive sleeve, the roller pin also having a surface adapted for engaging, the second end portion of the steering column assembly and for bearing against the second end portion during rotation of the steering column assembly so that the steering column assembly is suspended relative to the at least one support structure;

wherein the at least one optical scanning device is adapted to optically scan a feature of interest of the steering column assembly while a shaft of the steering column assembly is rotated for gathering data for identifying one or more deviations from one or more predetermined values for the feature of interest; and wherein, upon receiving and engaging the first end portion of the shaft of the steering column assembly, the headstock is adapted for actuation to translate it toward the roller pin so that the roller pin engages the second end portion of the steering column assembly and the steering column assembly is rotated while being scanned by the at least one optical scanning device.

3. The apparatus of claim 1, wherein the at least one support structure supports one or both of the tailstock and the at least one optical scanning device, the headstock and the tailstock are both present and one or both of the headstock or the tailstock are translatable along the at least one support structure relative to the other.

4. The apparatus of claim 1, wherein the at least one support structure includes an elongated base upon which the headstock is mounted, and to which one or both of the tailstock and the at least one optical scanning device is mounted.

5. The apparatus of claim 1, wherein the apparatus includes at least one intermediate support that is disposed between the drive sleeve and the roller pin and is adapted to be raised or lowered into and out of engagement with the steering column assembly for raising or lowering the steering column assembly and positioning it generally in opposing relationship with both the drive sleeve and the roller pin.

6. The apparatus of claim 2, wherein the roller pin adjoins a support adapted to receive the second end portion of the steering column assembly so that when the support receives the second end portion of the steering column assembly, the longitudinal axis of the steering column assembly is positioned at a height that is offset relative to a longitudinal axis of the roller pin.

7. The apparatus of claim 6, wherein the roller pin is positioned so that when the first end portion of the steering column assembly is received in the drive sleeve, and upon translation of the headstock in a direction toward the roller pin, the roller pin initially contacts the steering column assembly at a second end of the steering column assembly at a location offset from the longitudinal axis of the steering, column assembly and bears against the second end of the steering column assembly until the longitudinal axis of the steering column assembly is aligned generally with the longitudinal axis of the roller pin.

8. The apparatus of claim 1, wherein the drive sleeve includes an inner wall structure that includes a plurality of concentrically arranged hollow cylindrical and/or frusto-conical portions, each having a different diameter and being arranged with a progressively decreasing diameter along the longitudinal axis of the drive sleeve, with each hollow cylindrical portion and/or frusto-conical portion terminating at an edge portion that is adapted to engage an outer surface of a shaft of the steering column assembly at a location between the first end and the second end of the steering column assembly.

9. The apparatus of claim 1, wherein the drive sleeve is fabricated from a material that has a hardness that is less than the hardness of the portion of the steering column assembly that it engages.

10. The apparatus of claim 1, wherein the drive sleeve is made of a polymeric material.

11. The apparatus of claim 1, wherein the drive sleeve is adapted to receive and engage a plurality of different steering column assemblies, each having a first end portion including a shaft with a different diameter relative to each of the other steering column assemblies.

12. The apparatus of claim 1, wherein the at least one optical scanning device includes a laser beam emitter and a detector adapted to receive at least a portion of a laser beam that is reflected from the steering column assembly.

13. The apparatus of claim 1, wherein the at least one optical scanning device includes a laser beam emitter adapted for emitting a blue laser beam.

14. A steering column assembly system comprising the apparatus of claim 1 and a load cell adapted to detect the presence of a nonconforming steering column assembly that exhibits one or more deviations from the predetermined value and causes the operation of the apparatus to cease until the nonconforming steering column assembly is segregated from one or more steering column assemblies that are conforming.

15. The steering column assembly system of claim 14 wherein the apparatus, the load cell, or both, is contained within a substantially enclosed housing.

16. A method comprising steps of:
providing at least one steering column assembly designed to have a longitudinal axis and to include a first end portion and a second end portion, the first end portion including a shaft that is telescopically attached to a spline shaft portion, and a second end portion that includes a worm-wheel having a worm wheel face, the steering column assembly further including a sensor sleeve that is crimped onto the spline shaft portion to define a peripheral crimped joint and that is further joined for resisting rotational motion with at least one dimple;
rotating the steering column assembly about its longitudinal axis while scanning with at least one optical scanning device for one or more features of interest for the steering column assembly;
comparing data obtained about the one or more scanned features of interest with a predetermined value for the one or more scanned features of interest; and based upon the comparing step, identifying whether or not the steering column assembly conforms with the predetermined value.

17. The method of claim 16, wherein the method includes a step of scanning a reference steering column assembly for obtaining qualitative information about relative positions of a plurality of features of interest, without regard to dimensions of any of such features, for use thereafter in the cornparing step.

18. The method of claim 16, wherein the method includes repeating the steps for a plurality of steering column assemblies each being designed to have the same features, and based upon the identifying step, segregating one or more steering column assemblies that conform with the predetermined value from one or more steering column assemblies that do not conform with the predetermined value.

19. The method of claim 16, wherein the one or more features of interest for which scanning is performed are selected from:
   a. dimple location;
   b. dimple depth;
   c. dimple location relative to a groove in the spline shaft portion;
   d. sensor sleeve appearance;
   e. sensor sleeve runout:
   f. sensor sleeve peripheral crimp appearance;
   g. sensor sleeve crimp angle;
   h. distance from a location on the sensor sleeve to a shoulder on the spline shaft portion;
   i. location of a c-ring groove;
   j. distance of a c-ring groove relative to, a surface on the worm-wheel;
   k. position of the sensor sleeve relative to a worm-wheel surface;
   l. distance from a location on the sensor sleeve to a worm-wheel surface;
   m. location of the worm-wheel relative to a predetermined location in the spline shaft portion; or
   n. any combination of the foregoing.

20. The apparatus of claim 12, wherein the laser beam emitter is adapted for emitting a blue laser beam.

* * * * *

UNITED STATES PATENT AND TRADEMARK OFFICE
CERTIFICATE OF CORRECTION

PATENT NO. : 9,874,529 B2  
APPLICATION NO. : 15/116612  
DATED : January 23, 2018  
INVENTOR(S) : George Morrison, III et al.

Page 1 of 1

It is certified that error appears in the above-identified patent and that said Letters Patent is hereby corrected as shown below:

In the Claims

Column 21, Line 19: remove "engaging," and insert --engaging--

Column 21, Line 42: remove "stnicture" and insert --structure--

Column 22, Line 1: remove "steering," and insert --steering--

Column 24, Line 8: remove "to," and insert --to--

Signed and Sealed this  
Seventeenth Day of April, 2018

Andrei Iancu  
*Director of the United States Patent and Trademark Office*